(12) United States Patent
Takashima

(10) Patent No.: US 8,556,812 B2
(45) Date of Patent: Oct. 15, 2013

(54) BLOOD TESTING DEVICE

(75) Inventor: Tetsuya Takashima, Ehime (JP)

(73) Assignee: Panasonic Corporation, Osaka (JP)

( * ) Notice: Subject to any disclaimer, the term of this patent is extended or adjusted under 35 U.S.C. 154(b) by 461 days.

(21) Appl. No.: 12/919,333

(22) PCT Filed: Mar. 10, 2009

(86) PCT No.: PCT/JP2009/001077
§ 371 (c)(1),
(2), (4) Date: Aug. 25, 2010

(87) PCT Pub. No.: WO2009/113300
PCT Pub. Date: Sep. 17, 2009

(65) Prior Publication Data
US 2011/0004078 A1 Jan. 6, 2011

(30) Foreign Application Priority Data
Mar. 10, 2008 (JP) .................................. 2008-058950

(51) Int. Cl.
*A61B 5/00* (2006.01)
(52) U.S. Cl.
USPC .......................................... 600/309; 600/583
(58) Field of Classification Search
USPC .................................................. 600/309, 583
See application file for complete search history.

(56) References Cited

U.S. PATENT DOCUMENTS

| | | | |
|---|---|---|---|
| 6,506,168 B1 * | 1/2003 | Fathallah et al. | 600/578 |
| 2002/0130042 A1 | 9/2002 | Moerman et al. | |
| 2003/0116583 A1 * | 6/2003 | Pugh | 221/268 |
| 2010/0042016 A1 | 2/2010 | Akiyama | |
| 2010/0185118 A1 | 7/2010 | Takashima et al. | |
| 2010/0222703 A1 * | 9/2010 | Takashima et al. | 600/583 |

FOREIGN PATENT DOCUMENTS

| | | |
|---|---|---|
| JP | 2003-524496 | 8/2003 |
| JP | 2003-534088 | 11/2003 |
| JP | 2004-519302 | 7/2004 |
| WO | 02/078533 | 10/2002 |
| WO | 2009/019854 | 2/2009 |

OTHER PUBLICATIONS

U.S. Appl. No. 12/866,308 to Masahiro Kitagawa et al., filed Aug. 5, 2010.

U.S. Appl. No. 12/671,708 to Tetsuya Takashima et al., filed Feb. 2, 2010.

* cited by examiner

*Primary Examiner* — Clayton E Laballe
*Assistant Examiner* — Noam Reisner
(74) *Attorney, Agent, or Firm* — Greenblum & Bernstein, P.L.C.

(57) ABSTRACT

A blood testing device in which a blood sensor does not contaminate a piercing section when discarded. The blood testing device (11) is provided with the piercing section (13) having an upper holder (13a) and a lower holder (13b), and also with a connector (18). In piercing operation, the connector (18), the upper holder (13a), and the lower holder (13b) sandwich and hold the sensor (24). To discharge the sensor, the lower holder (13b) is pivoted so as to be separated from the upper holder (13a), which creates a space between the lower holder (13b) and the upper holder (13a) to expose the sensor (24).

21 Claims, 40 Drawing Sheets

BLOOD TESTING DEVICE

TECHNICAL FIELD

The present invention relates to a blood test apparatus that tests blood by puncturing skin and so forth.

BACKGROUND ART

The blood test apparatuses disclosed in Patent Document 1 and Patent Document 2 have been known as conventional blood test apparatuses.

FIG. 1 shows a drawing showing a configuration of conventional blood test apparatus 1.

As shown in FIG. 1, blood test apparatus 1 includes housing 3 having an approximately rectangular solid shape. Housing 3 has puncturing section 2, needle puncturing unit 4 provided to face puncturing section 2, sensor cartridge 6 in which blood sensors (hereinafter "sensors") 5 are stacked and stored, conveying section 7 that conveys sensors 5 stored in sensor cartridge 6 to puncturing section 2 and electrical circuit section 8 electrically connected to sensor 5 conveyed to puncturing section 2.

Now, a test method using blood test apparatus 1 configured as described above will be explained.

FIG. 2 is a flowchart showing the test method using blood test apparatus 1.

First, in step S11, the user contacts blood test apparatus 1 with finger 9a (see FIG. 1) to be tested.

In step 12, the user presses puncturing button 4b. Puncturing needle 4a is ejected from needle puncturing unit 4 by pressing puncturing button 4b and punctures skin 9. Blood 10 exudes by puncturing skin 9.

In step S13, the user presses conveying button 7b. By pressing conveying button 7b, the bottom sensor 5 among sensors stored in sensor cartridge 6 is conveyed to puncturing section 2. Sensor 5 conveyed to puncturing section 2 takes blood 10 exuding from skin 9 inside.

In step S14, electrical circuit section 8 measures the properties of blood 10 taken in sensor 5.

In step S15, the user removes sensor 5 stained with blood 10 from puncturing section 2 and discards it.

Patent Document 1: Published Japanese Translation of PCT Application No. 2004-519302

Patent Document 2: Published Japanese Translation of PCT Application No. 2003-524496

DISCLOSURE OF INVENTION

Problems to be Solved by the Invention

However, this conventional blood test apparatus 1 is not sanitary, because, when sensor 5 stained with blood 10 is removed from puncturing section 2 and discarded, puncturing section 2, its neighboring parts, fingers and so forth are likely to be stained with blood 10 having adhered to sensor 5.

It is therefore an object of the present invention to provide a blood test apparatus that does not stain a puncturing section when a blood sensor is discarded.

Means for Solving the Problem

The blood test apparatus according to the present invention adopts a configuration to include: a holding section composed of a first holder and a second holder that sandwich and hold a blood sensor; a puncturing section that punctures skin from the first holder side of the blood sensor held by the holding section; and an ejecting section that rotates the second holder to part from the first holder and forms a space between the first holder and the second holder by the rotation to expose the blood sensor.

The blood test apparatus according to the present invention adopts a configuration to include: a holding section in which a blood sensor is inserted and held; a puncturing section that punctures skins from a side of the blood sensor held by the holding section; a holder that is arranged to face the blood sensor and has a finger holding section; and an ejecting section that rotates the holder to part from the blood sensor and forms a space between the blood sensor and the holder to expose the blood sensor.

Advantageous Effects of Invention

According to the present invention, an ejecting section is provided to rotate a second holder to part from the first holder and form a space between the first holder and the second holder by this rotation when a sensor is ejected. Therefore, it is possible to eject a blood sensor without allowing contact of blood and so forth having adhered to the blood sensor with a puncturing section, so that it is possible to keep the inside of the apparatus including the puncturing section clean.

In addition, since a blood sensor is ejected using an ejecting means, fingers are not stained with blood and kept clean, so that sanitation and safety are provided.

BEST MODE FOR CARRYING OUT THE INVENTION

Now, embodiments of the present invention will be described in detail with reference to the accompanying drawings.

Embodiment 1

Figure 1:
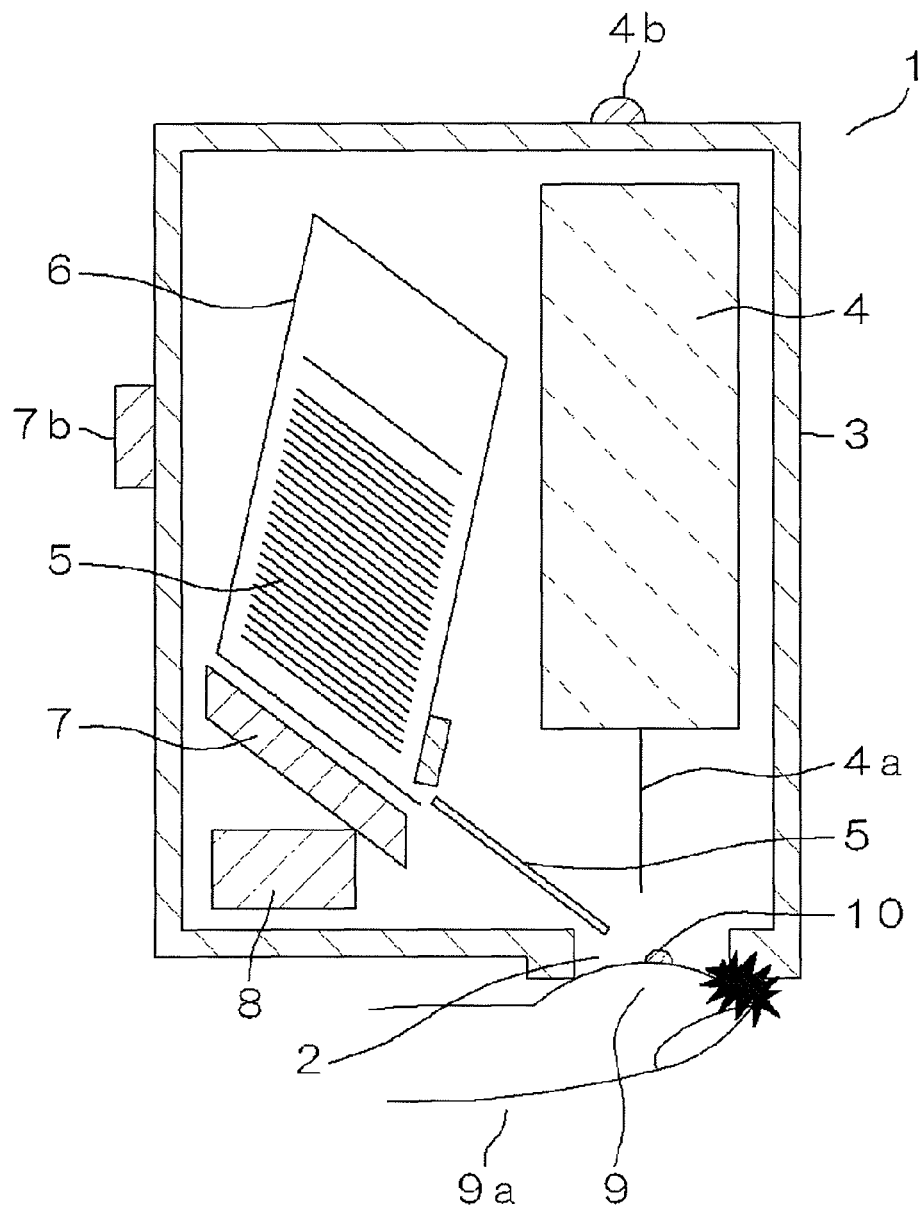
FIG. 1 is a drawing showing a configuration of a conventional blood test apparatus.
Figure 2:
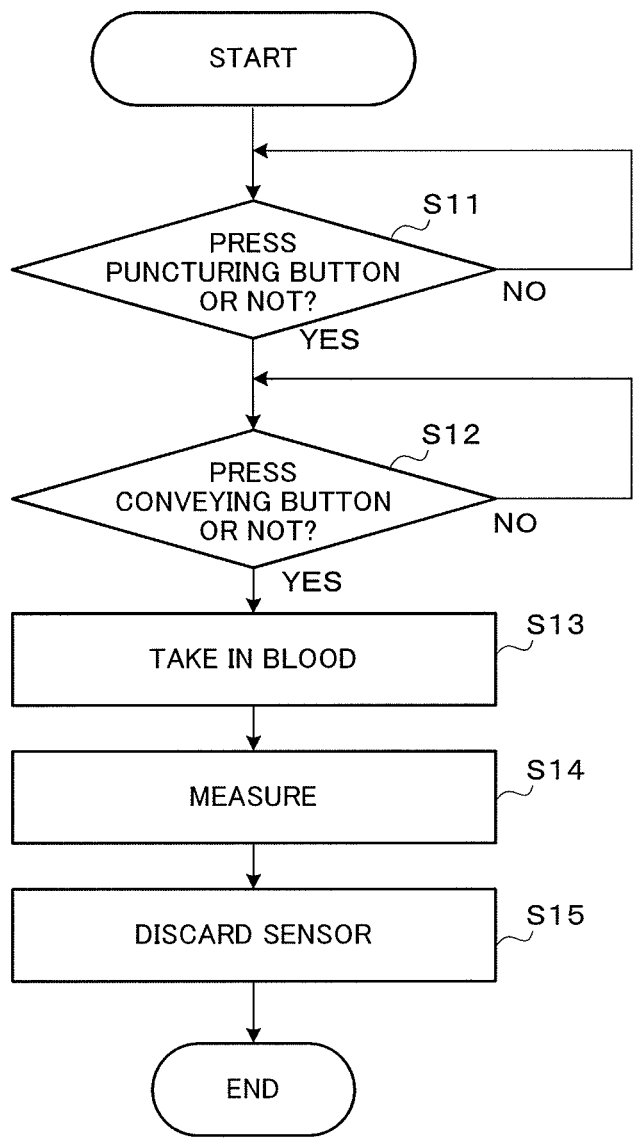
FIG. 2 is a flowchart showing a test method using the conventional blood test apparatus.
Figure 3A:
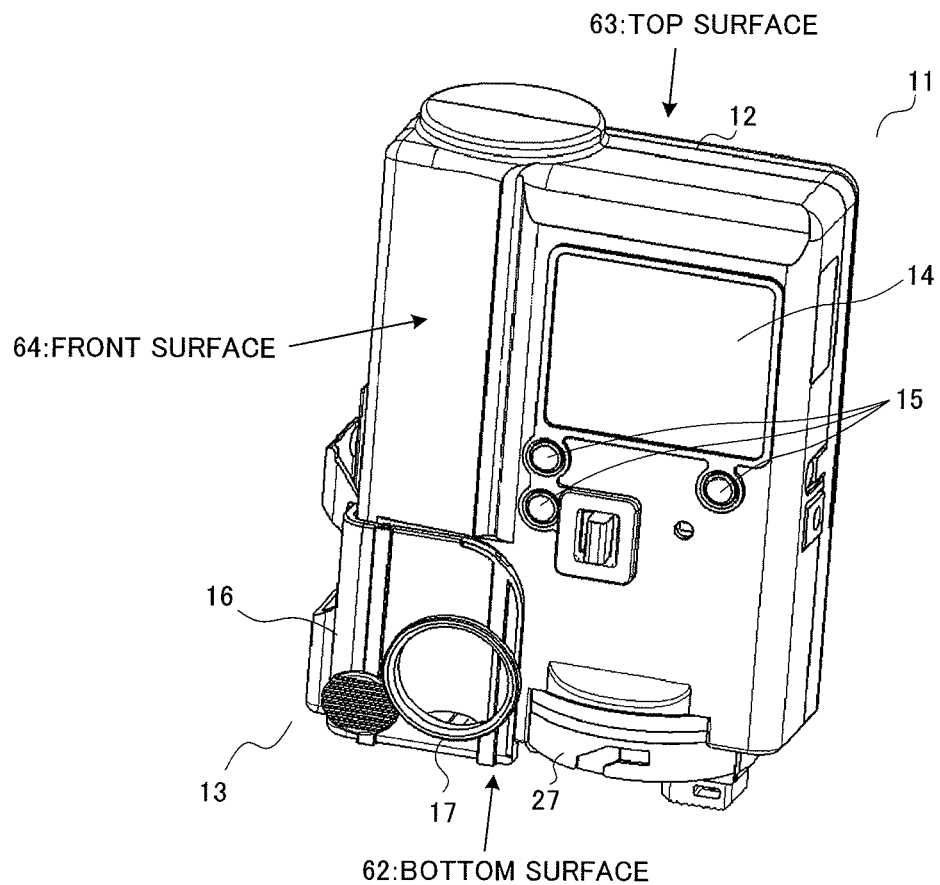
FIG. 3A is an external perspective view of a blood test apparatus according to Embodiment 1 of the present invention not in use.
Figure 3B:
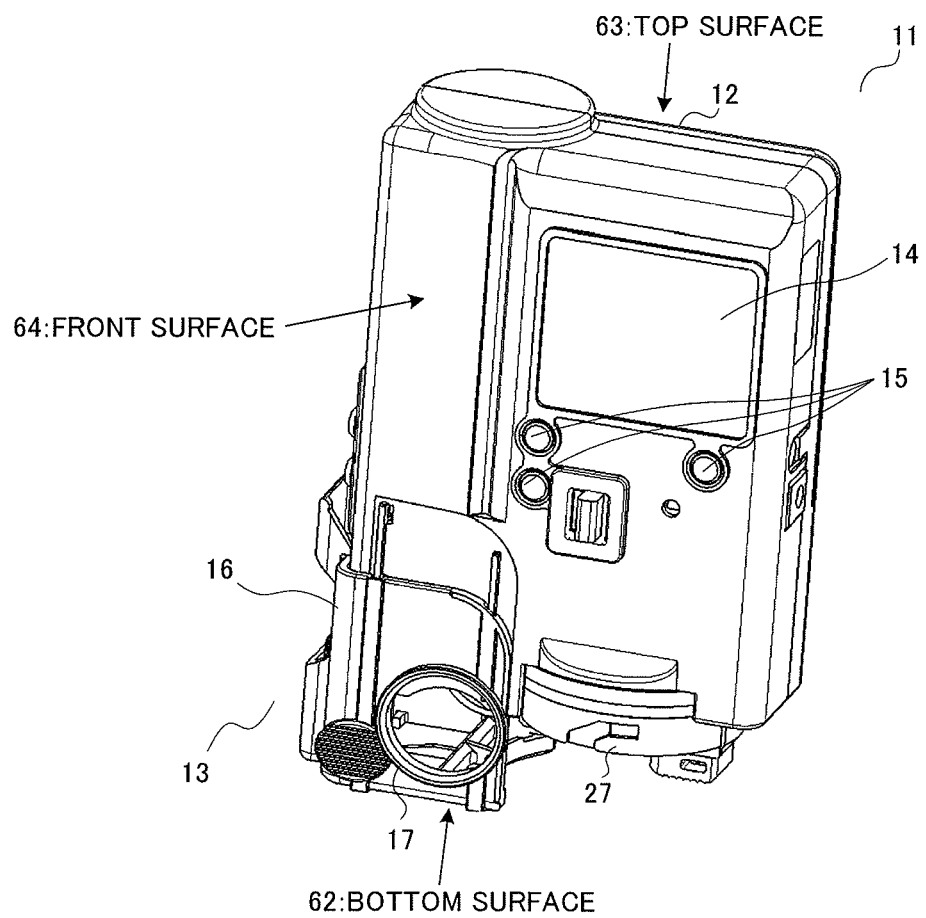
FIG. 3B is an external perspective view of the blood test apparatus according to Embodiment 1 in use.

FIG. 3 is an external perspective view of a blood test apparatus according to Embodiment 1 of the present invention. FIG. 3A shows the blood test apparatus not in use and FIG. 3B shows the blood test apparatus in use.

As shown in FIG. 3A and FIG. 3B, blood test apparatus 11 has housing 12 made of resin and having an approximately rectangular solid shape. Puncturing section 13 is mounted around a corner (lower left side in FIG. 3A and FIG. 3B) of housing 12. Sensor cartridge 27 part of which (lower right side in FIG. 3A and FIG. 3B) is exposed outside is mounted in housing 12. Here, in the approximately rectangular solid shape, the surface on which sensor cartridge 27 is mounted is bottom surface 62 (bottom surface) and the surface to face this bottom surface 62 is top surface 63. On the front surface 64 side of housing 64, display section 14 configured by a LCD (liquid crystal display) and so forth is provided and various operation switches 15 are provided below display section 14.

Puncturing section 13 has cover 16 that covers the exterior of the corners of the sides of housing 12 and slides downward along the exterior. Finger inserting hole 17 is open in the front surface of cover 16.

As shown in FIG. 3A, in an unused state, cover 16 is raised and the exterior of housing 12 is located in the position of finger inserting hole 17, so that it is not possible to insert a finger in finger inserting hole 17.

As shown in FIG. 3B, finger inserting hole 17 is located apart from the exterior of housing 12 by coming down cover 16 when the apparatus is used. By this means, it is possible to insert a finger in finger inserting hole 17, and therefore, it is possible to puncture the inserted finger.

Figure 4:
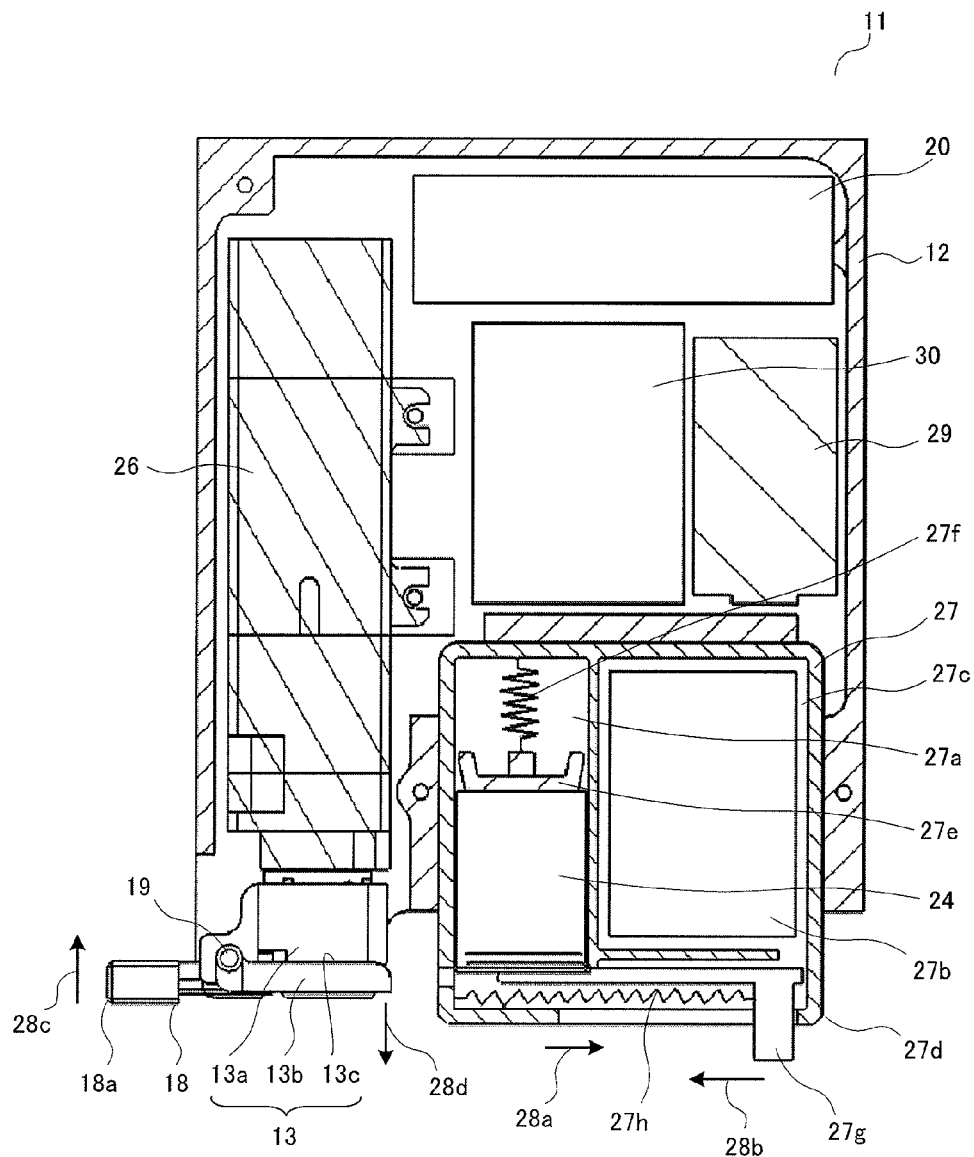
FIG. 4 is a cross sectional view of the blood test apparatus according to Embodiment 1.

FIG. 4 is a cross sectional view of blood test apparatus 11 when cover 16 is removed.

As shown in FIG. 4, puncturing section 13 is mounted in a lower corner of housing 12. Puncturing section 13 is composed of upper holder 13a and lower holder 13b, and sandwiches and fixes blood sensor (hereinafter "sensor") 24 between upper holder 13a and lower holder 13b. Here, in FIG.

4, since sensor 24 is sandwiched between upper holder 13a and lower holder 13b, sensor 24 is not shown in the figure. With the present embodiment, upper holder 13a constitutes a puncturing means.

The present embodiment is characterized by inserting and holding sensor 24 and having connector 18 electrically connected with connection electrodes 43a to 45a and 47a (see FIG. 17) in sensor 24. Connector 18 has ejection button 18a that is pressed to eject sensor 24 at the time of ejecting (discarding) sensor 24.

Connector 18 is pivotably mounted on rotating shaft 19 provided in the lower edge part of housing 12. Ejection button 18a of connector 18 rotates upward (the direction of arrow 28c) about rotating shaft 19.

In addition to connector 18, lower holder 13b is pivotably mounted on rotating shaft 19. The sensor inserting inlet 13c side, which is the sensor cartridge 27 side, of lower holder 13b rotates downward (in the direction of arrow 28d) about rotating shaft 19. The sensor inserting inlet 13c side of lower holder 13b is rotated downward by rotating ejection button 18a in connector 18 upward (in the direction of arrow 28c). Here, as described later with FIG. 5, the angle of downward (in the direction of arrow 28d) rotation of the sensor inserting inlet 13c side of lower holder 13b is greater than the angle of upward (in the direction of arrow 28c) rotation of ejecting bottom 18a in connector 18.

Laser puncturing unit 26 (used as an exemplary puncturing means) is mounted to face puncturing section 13. Here, it is possible to use a needle puncturing unit using a puncture needle as a puncturing means.

Sensor cartridge 27 is removably inserted in the lower part of housing 12 next to puncturing section 13.

Sensor cartridge 27 is composed of sensor chamber 27a in which sensors 24 are stacked and stored, desiccant chamber 27c in which desiccant 27b is stored and conveying section 27d that conveys the bottom sensor 24 stored in sensor chamber 27a to puncturing section 13.

Sensors 24 stacked and stored in sensor chamber 27a are pressed downward by pressing member 27e. Pressing member 27e is biased downward by spring 27f. Desiccant 27b is stored to dry the inside of sensor chamber 27a and prevents deterioration of sensors 24. Conveying section 27d is composed of slide plate 27g that conveys sensor 24 stored on the bottom to puncturing section 13 and spring 27h that biases slide plate 27g in the direction of arrow 28a.

Negative pressure means 29 is provided above sensor cartridge 27. Negative pressure means 29 is composed of a motor and a vacuum pump coupled to this motor. A negative pressure generated in the vacuum pump is supplied to negative pressure chamber 29a (see FIG. 15A) formed in lower holder 13b. Negative pressure means 29 makes skin 9 (see FIG. 15A) swell by creating a negative pressure in puncturing section 13 at the time skin 9 is punctured.

Electrical circuit section 30 is accommodated between negative pressure means 29 and laser puncturing unit 26. Electrical circuit section 30 measures the blood sugar level and so forth, controls laser puncturing unit 26 and controls negative pressure means 29, based on signals transmitted from sensor 24. Battery 20 is accommodated next to electrical circuit section 30 and negative pressure means 29. Battery 20 supplies power to each of those parts. Battery 20 is provided to be removably inserted in housing 12.

Now, operations of blood test apparatus 11 configured as described above will be explained.

First, puncturing operations of blood test apparatus 11 will be described.

As shown in FIG. 4, the user first slides slide plate 27g in the direction of arrow 28b. As a result of this, sensor 24 is set between upper holder 13a and lower holder 13b in puncturing section 13. Next, the user contacts lower holder 13b in puncturing section 13 with skin 9 to sample blood from. In this state, the user presses puncturing button 26j (see FIG. 22). Laser light 26h (see FIG. 21) is emitted from laser puncturing unit 26 and punctures skin 9. Blood exudes from skin 9. Blood is taken into sensor 24 and chemically reacts in sensor 24, and the result is transmitted to electrical circuit section 30. Electrical circuit section 30 measures the blood sugar level and so forth based on signals transmitted from sensor 24. Electrical circuit section 30 displays the measurement result on display section 14 (see FIG. 3).

The present embodiment is characterized by the sensor ejecting operation by pivotably moving lower holder 13b and connector 18. Now, operations at the time a sensor is ejected will be explained with reference to FIG. 5 to FIG. 16.

FIG. 4 shows a state during or immediately after measurement, that is, a state in which a finger touches lower holder 13b. The state shown in FIG. 4 is referred to as the first state.

Figure 5:
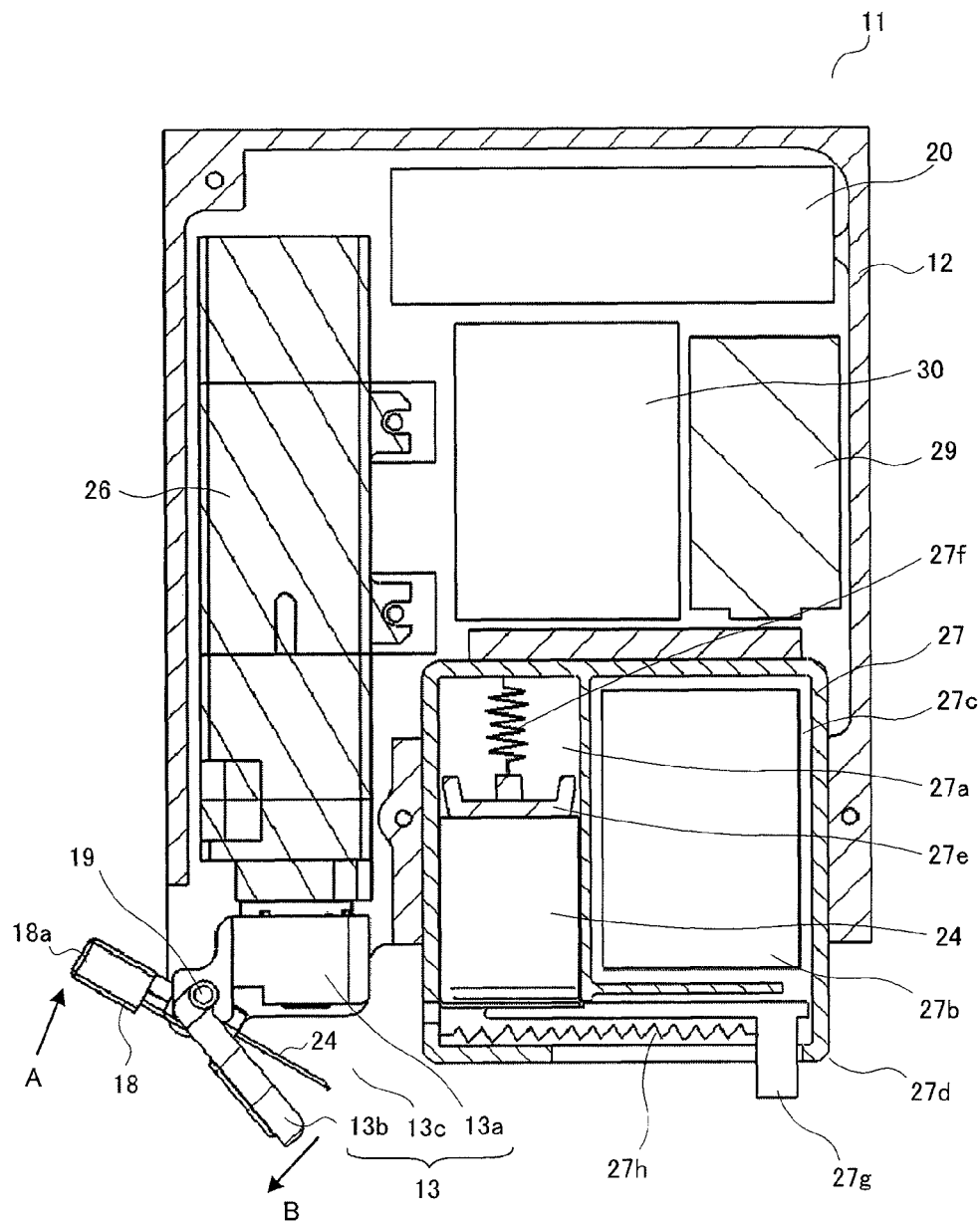
FIG. 5 is a cross sectional view of the blood test apparatus according to Embodiment 1 when a sensor is ejected.
Figure 6:
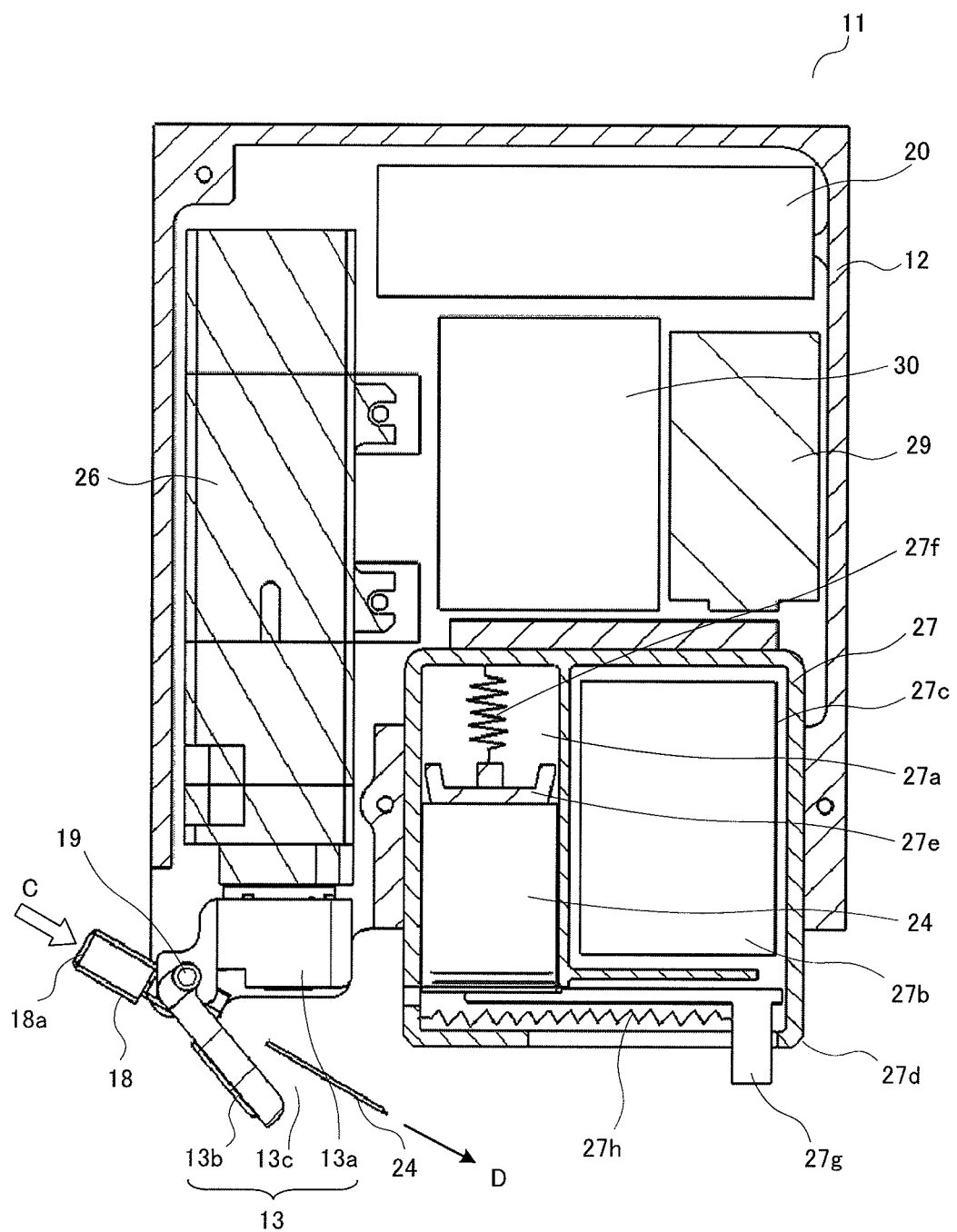
FIG. 6 is a cross sectional view of the blood test apparatus according to Embodiment 1 when a sensor is ejected.

FIG. 5 and FIG. 6 are cross sectional views showing the blood test apparatus at the time of ejecting a sensor. FIG. 5 shows a second state and FIG. 6 shows a third state.

[Sensor Ejecting (Discarding) Operation 1]

First, as shown in FIG. 5, the user moves ejection button 18a in connector 18 in the direction of arrow A. Then, connector 18 holding sensor 24 rotates about rotating shaft 19 in the direction of arrow A and lower holder 13b rotates in the direction of arrow B opposite to arrow A in conjunction with the rotation of connector 18. At this time, the lock to lower holder 13b is released (described laser in detail) due to the rotation of connector 18 and lower holder 13b rotates at an angle equal to or greater than the angle of rotation of connector 18. That is, connector 18 sandwiches and holds sensor 24, and therefore, when connector 18 rotates, the held sensor 24 also rotates in the direction of arrow B, so that the angle to eject sensor 24 is the same as the angle of rotation of connector 18. As shown in FIG. 5, lower holder 13b rotates at the angle twice as large as this angle to eject sensor 24, and therefore, is opened widely from upper holder 13a. Since large spaces are formed on the top and bottom surfaces of sensor 24, an advantage of easily ejecting (discarding) sensor 24 is provided and adhesion of blood to upper holder 13a and lower holder 13b is effectively prevented.

[Sensor Ejecting (Discarding) Operation 2]

Next, as shown in FIG. 6, the user presses ejection button 18a in connector 18 in the direction of arrow C. As a result of this, sensor 24 held by connector 18 is pushed out in the direction of arrow D. Measurement of the blood sugar level and so forth is finished and sensor 24 with blood is ejected downward from housing 12. The user can eject sensor 24 without touching puncturing section 13 and so forth.

After sensor 24 is discarded, the user puts back the cover (see FIG. 3) to a predetermined position, so that connector 18 and lower holder 13b return to respective original positions.

As described above, it is possible to eject sensor 24 without staining puncturing section 13 and sensor cartridge 27 placed in the vicinity of puncturing section 13 with blood having adhered to sensor 24 by ejecting sensor 24 having been inserted in puncturing section 13 to the sensor cartridge 27 side, so that it is possible to keep puncturing section 13 and its neighborhood clean.

In addition, sensor 24 with blood is ejected by pressing ejection button 18a in connector 18 in the direction of arrow C, so that the punctured finger is not stained and kept clean.

With the present embodiment, in particular, connector 18 and lower holder 13b are separately provided, and when a sensor is ejected (discarded), lower holder 13b is opened by the rotation of connector 18 at an angle greater than the angle of rotation of connector 18, so that it is possible to further improve the above-described effect of preventing puncturing section 13 and so froth from being stained.

Next, sensor ejecting (discarding) operations of lower holder 13b will be explained in detail with reference to FIG. 7 to FIG. 16.

FIG. 7 to FIG. 10 are perspective views of upper holder 13a, lower holder 13b and connector 18.

Figure 7A:
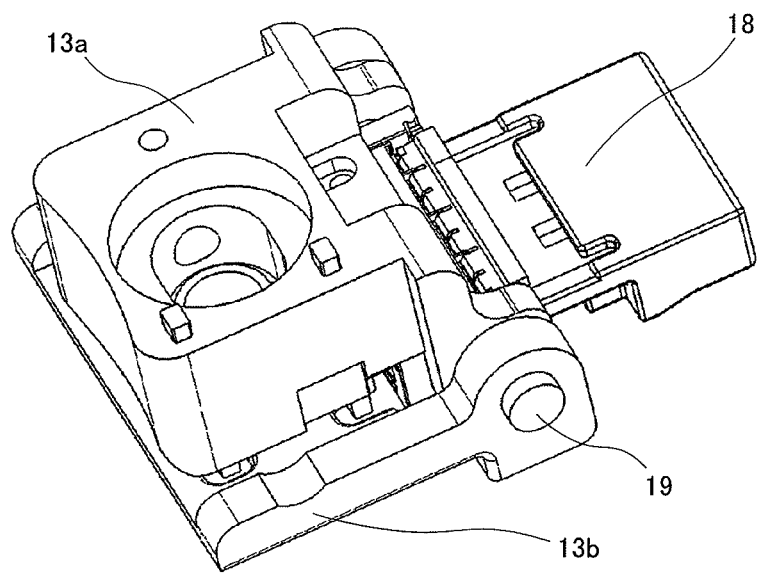
FIG. 7 is a perspective view showing an upper holder, a lower holder and a connector in the blood test apparatus according to Embodiment 1.

FIG. 7 shows a state of upper holder 13a, lower holder 13b and connector 18 during or immediately after measurement (a state in which a finger touches lower holder 13b). In this state in which the sensor is held, sensor 24 is inserted and held in connector 18, and electrically connected to connector 18.

Figure 7B:
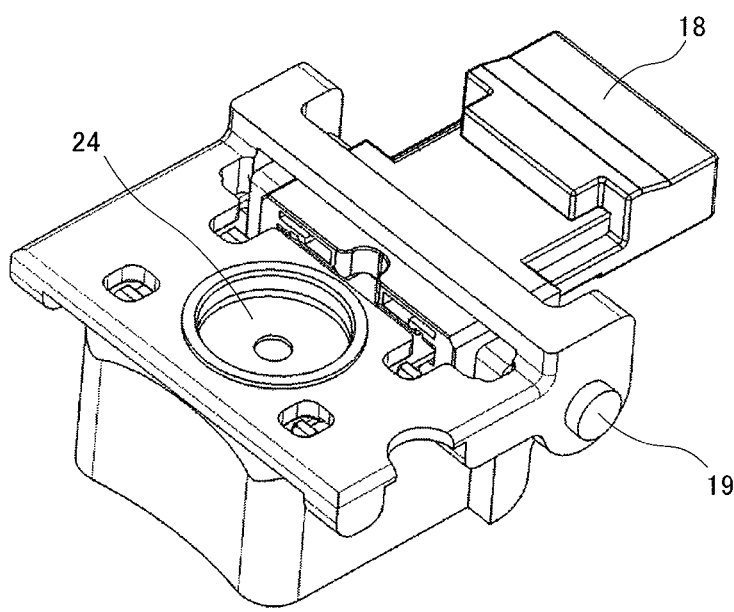

As shown in FIG. 7B, sensor 24 is sandwiched between upper holder 13a and lower holder 13b and seen from the hole in lower holder 13b. In addition, connector 18 and lower holder 13b are mounted on rotating shaft 19 to be able to rotate about rotating shaft 19.

Figure 8A:
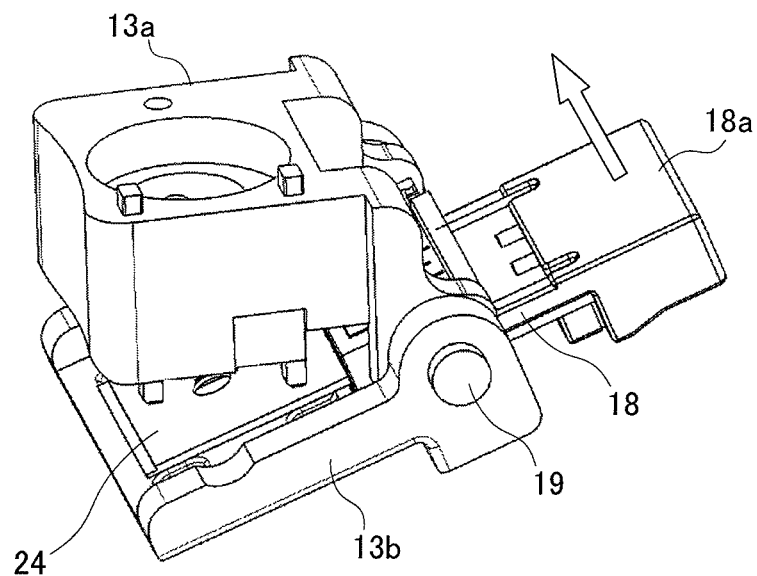
FIG. 8 is a perspective view showing an upper holder, a lower holder and a connector in the blood test apparatus according to Embodiment 1.
Figure 8B:
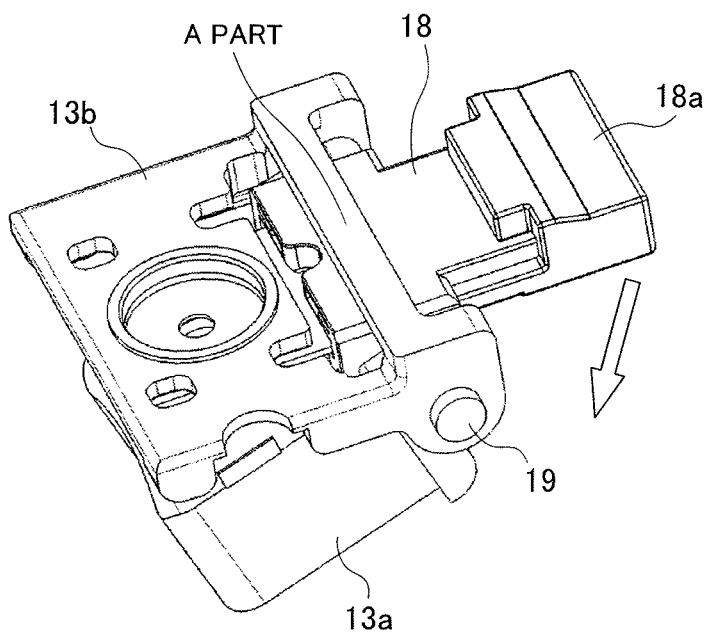

FIG. 8 is a perspective view showing a state of the above-described "[sensor ejecting (discarding) operation 1-1]". FIG. 8A is a perspective view from the top surface (the holder 13a side) and FIG. 8B is a perspective view from the bottom surface (the lower holder 13b side).

As shown in FIG. 8A, the user lifts ejection button 18a in connector 18 in the direction of the arrow. Seeing from the bottom surface, this movement makes ejection button 18a in connector 18 lower in the direction of the arrow as shown in FIG. 8B.

When connector 18 is rotated, A part (see FIG. 8B) in lower holder 13b is pushed by the rotation of connector 18 and rotates. By this means, a space is formed above the top surface of sensor 24 (the upper holder 13a side) as shown in FIG. 8A.

Figure 9A:
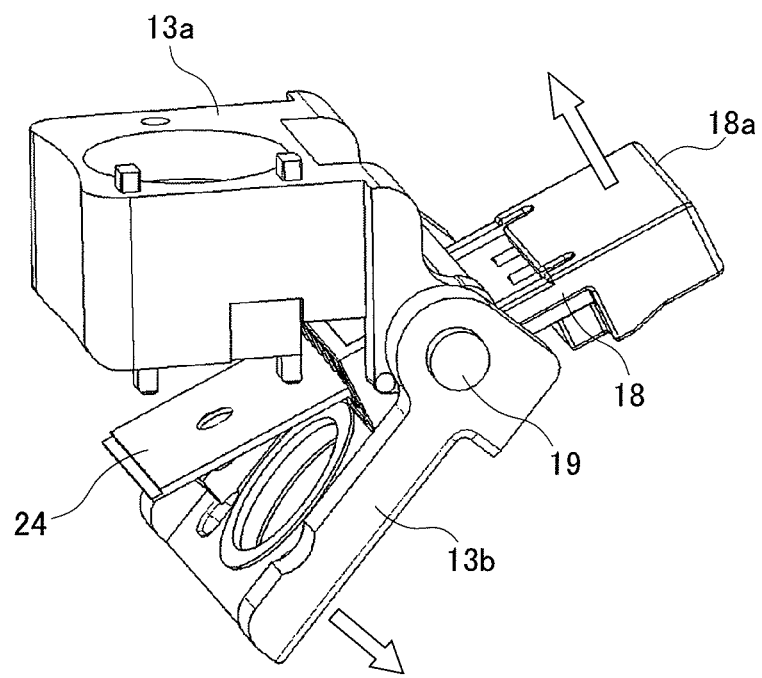
FIG. 9 is a perspective view showing an upper holder, a lower holder and a connector in the blood test apparatus according to Embodiment 1.
Figure 9B:
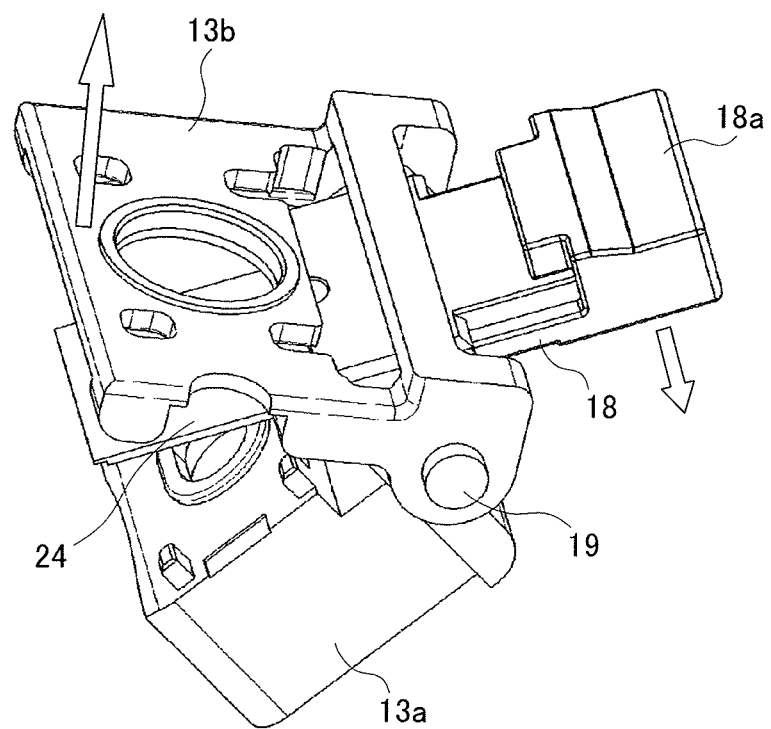

FIG. 9 is a perspective view showing a state of the above-described "[sensor ejecting (discarding) operation 1-2]", FIG. 9A is a perspective view from the top surface and FIG. 9B is a perspective view from the bottom surface.

As shown in FIG. 9A, the user further lifts ejection button 18a in connector 18 in the direction of the arrow. When lower holder 13b rotates at an angle equal to or greater than a certain angle, the lock to upper holder 13a is released (described later) and lower holder 13b rotates at an angle equal to or greater than the angle of rotation of connector 18. By this means, a space is formed below the bottom surface of sensor 24 (the lower holder 13b side) as shown in FIG. 9B.

Figure 10:
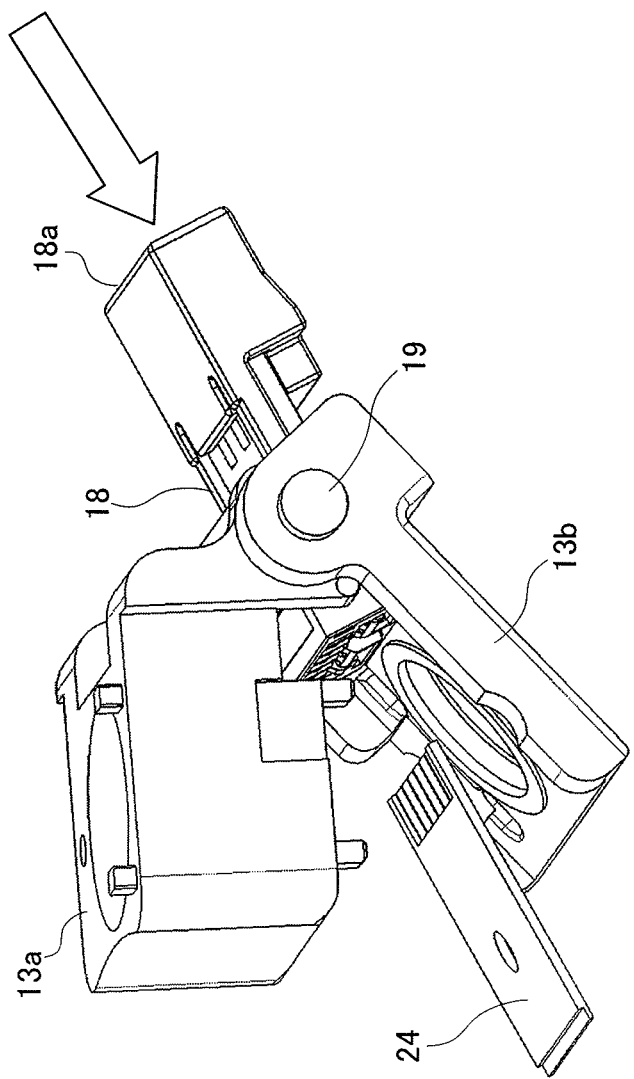
FIG. 10 is a perspective view showing an upper holder, a lower holder and a connector in the blood test apparatus according to Embodiment 1.

FIG. 10 shows a state of the above-described "[sensor ejecting (discarding) operation 2]".

As indicated by the arrow in FIG. 10, the user pushes ejection button 18a in connector 18 in a state in which spaces are formed above and below the upper and bottom surfaces of sensor 24, respectively. By this means, sensor 24 is ejected so as to be pushed out from connector 18. Since wide spaces are formed above and below the upper and bottom surfaces of sensor 24, respectively, blood having adhered to sensor 24 does not adhere to upper holder 13a and lower holder 13b.

Figure 11A:
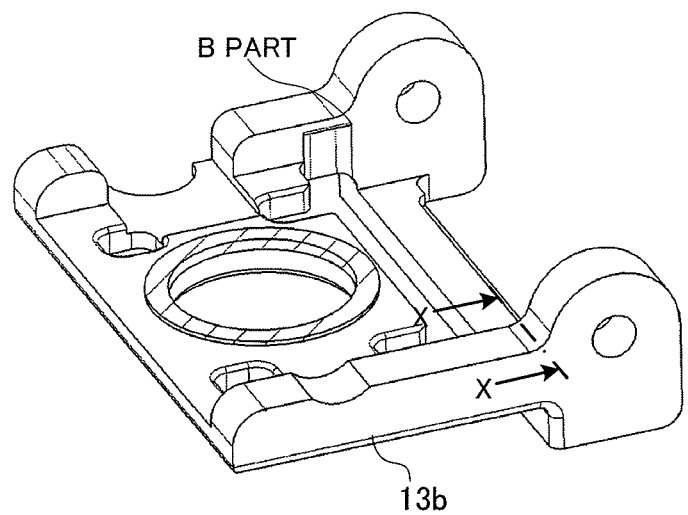
FIG. 11A is a perspective view showing the lower holder in the blood test apparatus according to Embodiment 1 from the top surface.
Figure 11B:
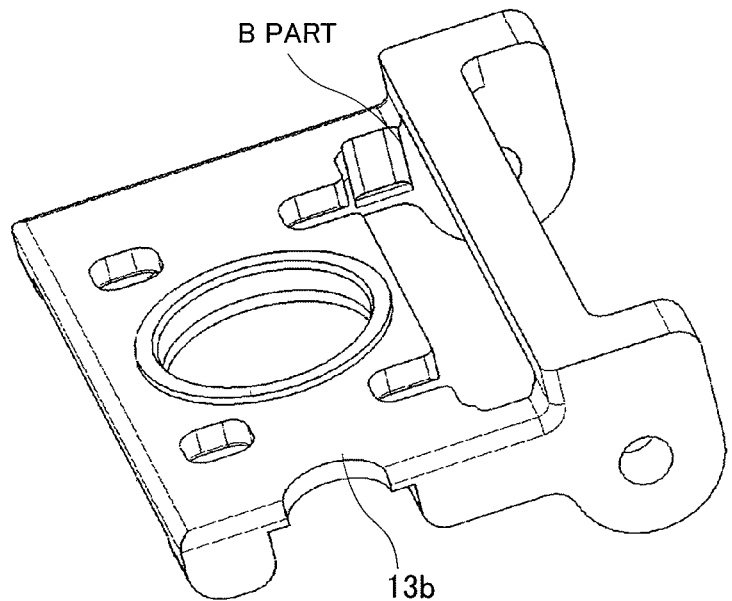
FIG. 11B is a perspective view showing the lower holder in the blood test apparatus according to Embodiment 1 from the bottom surface.
Figure 11C:
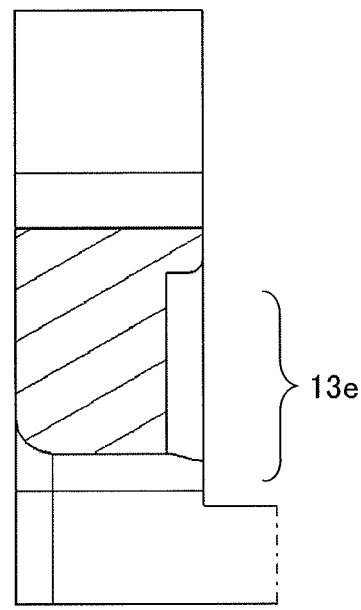
FIG. 11C is a cross sectional view of the lower holder seen from an X-X arrow in FIG. 11A.

FIG. 11A to FIG. 11C are perspective views of lower holder 13b. FIG. 11A is a perspective view from the top surface, FIG. 11B is a perspective view from the bottom surface and FIG. 11C is a cross sectional view of the lower holder seen from an X-X arrow in FIG. 11A.

As shown in FIG. 11C, cutout part 13e is provided in B part in lower holder 13b.

Figure 12:
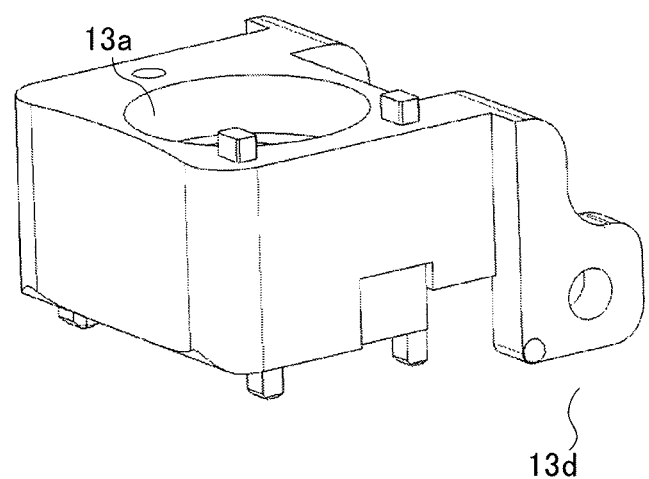
FIG. 12 is a perspective view of an upper holder in the blood test apparatus according to Embodiment 1.

FIG. 12 is a perspective view of upper holder 13a.

As shown in FIG. 12, projecting part 13d fitting in cutout part 13e in lower holder 13b is provided in upper holder 13a.

Figure 13A:
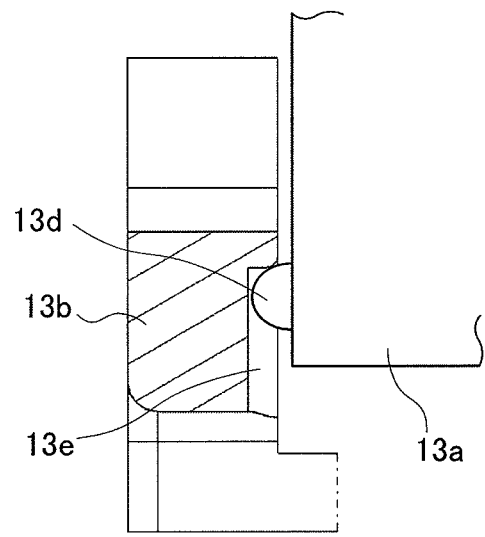
FIG. 13A is a cross sectional view of primary parts showing movement of the lower holder in the blood test apparatus according to Embodiment 1.
Figure 13B:
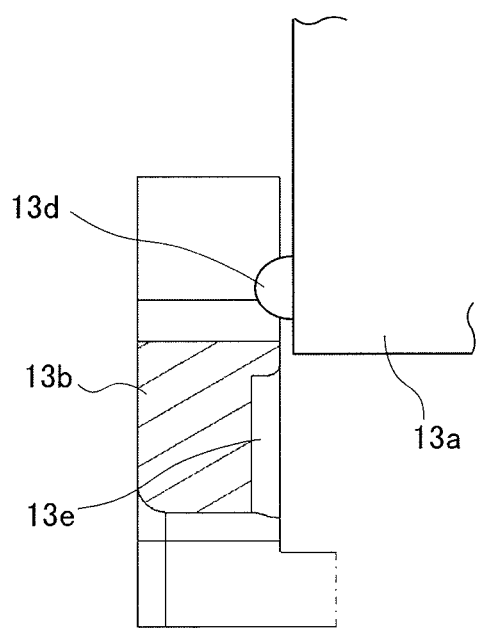
FIG. 13B is a cross sectional view of primary parts showing movement of the lower holder in the blood test apparatus according to Embodiment 1.

FIG. 13A and FIG. 13B are cross sectional view of primary parts showing operations of lower holder 13b. FIG. 13A shows a state in which projecting part 13d in upper holder 13a is fitted in cutout part 13e in lower holder 13b. FIG. 13B shows a state in which cutout part 13e in lower holder 13b climbs over projecting part 13d in upper holder 13a.

As shown in FIG. 13A, movement of lower holder 13b is limited by fitting projecting part 13d in upper holder 13a in cutout part 13e in lower holder 13b. FIG. 13A shows the state of operations from sensor insertion to sensor disposal (until spaces are formed between the sensor and the upper holder). At this time, connector 18 has rotated at a certain angle.

FIG. 13B shows the state in which connector 18 is rotated to a predetermined position (sensor ejecting position).

When cutout section 13e in lower holder 13b climbs over projecting section 13d in upper holder 13a, lower holder 13b comes down due to its own weight. Lower holder 13b rotates at the rotation angle equal to or greater than the angle of rotation of connector 18, so that a space is formed between sensor 24 and lower holder 13b. In this state, when the user pushes up cover 16 (see FIG. 3) of the apparatus body, lower holder 13b is pushed up by the projecting part (not shown) provided in cover 16, so that the state is returned to the state in which the sensor is inserted (see FIG. 13A).

Figure 14:
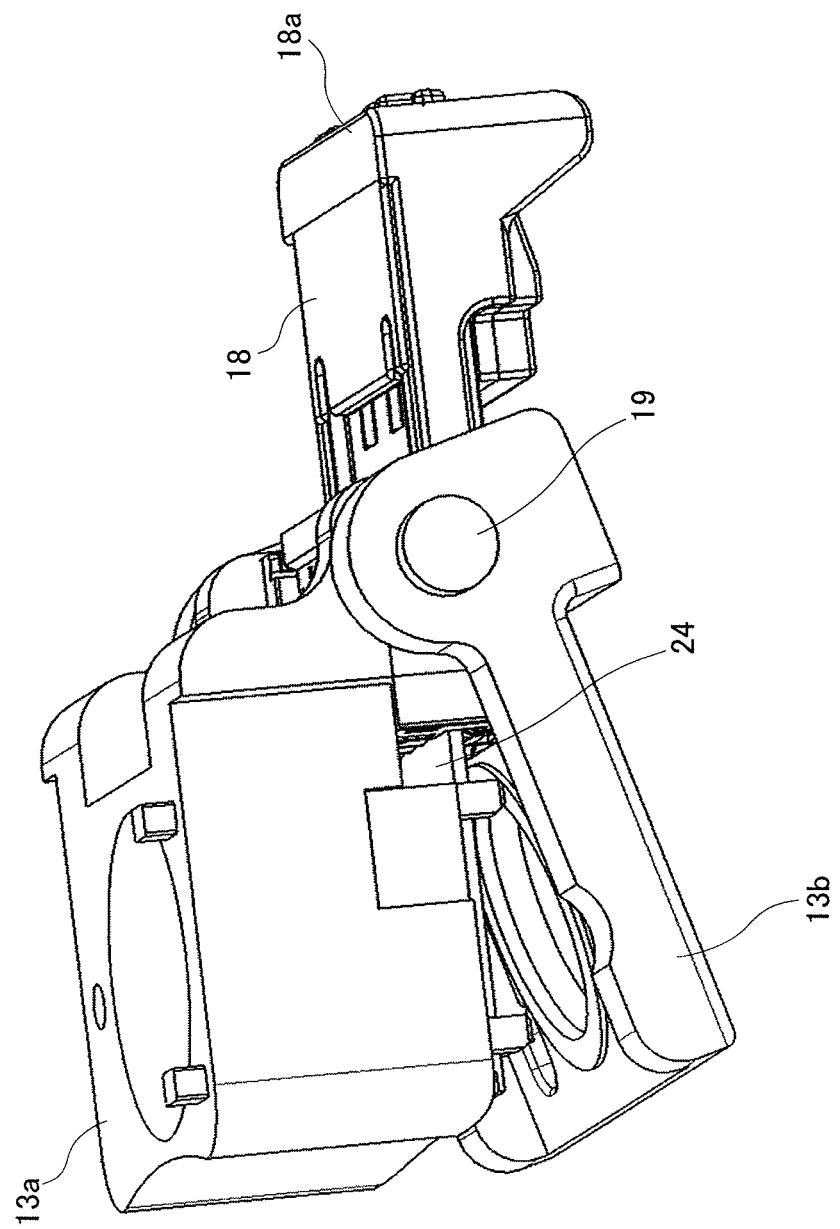
FIG. 14 is a perspective view showing the upper holder, the lower holder and the connector in the blood test apparatus according to Embodiment 1.

FIG. 14 is a perspective view of upper holder 13a, lower holder 13b and connector 18.

FIG. 14 shows a state in which sensor 24 is inserted between upper holder 13a and lower holder 13b. As for the relationship between projecting part 13d in upper holder 13a and cutout part 13e in lower holder 13b, usually, a state is provided where projecting part 13d in upper holder 13a contacts an end part of cutout part 13e in lower holder 13b, that is, lower holder 13b is a little open. This configuration provides an advantage of easy insertion of sensor 24.

Here, the force to open lower holder 13b is generated by a configuration in which a spring is provided between upper holder 13a and lower holder 13b and a configuration in which lower holder 13b comes down by its own weight. In FIG. 14, the configuration in which lower holder 13b comes down by its own weight is employed.

In measurement, the user uses the apparatus by lifting lower holder 13b with a finger and pushes the finger against lower holder 13b. Lower holder 13b is preferably lifted so as to be parallel to sensor 24.

Figure 15A:
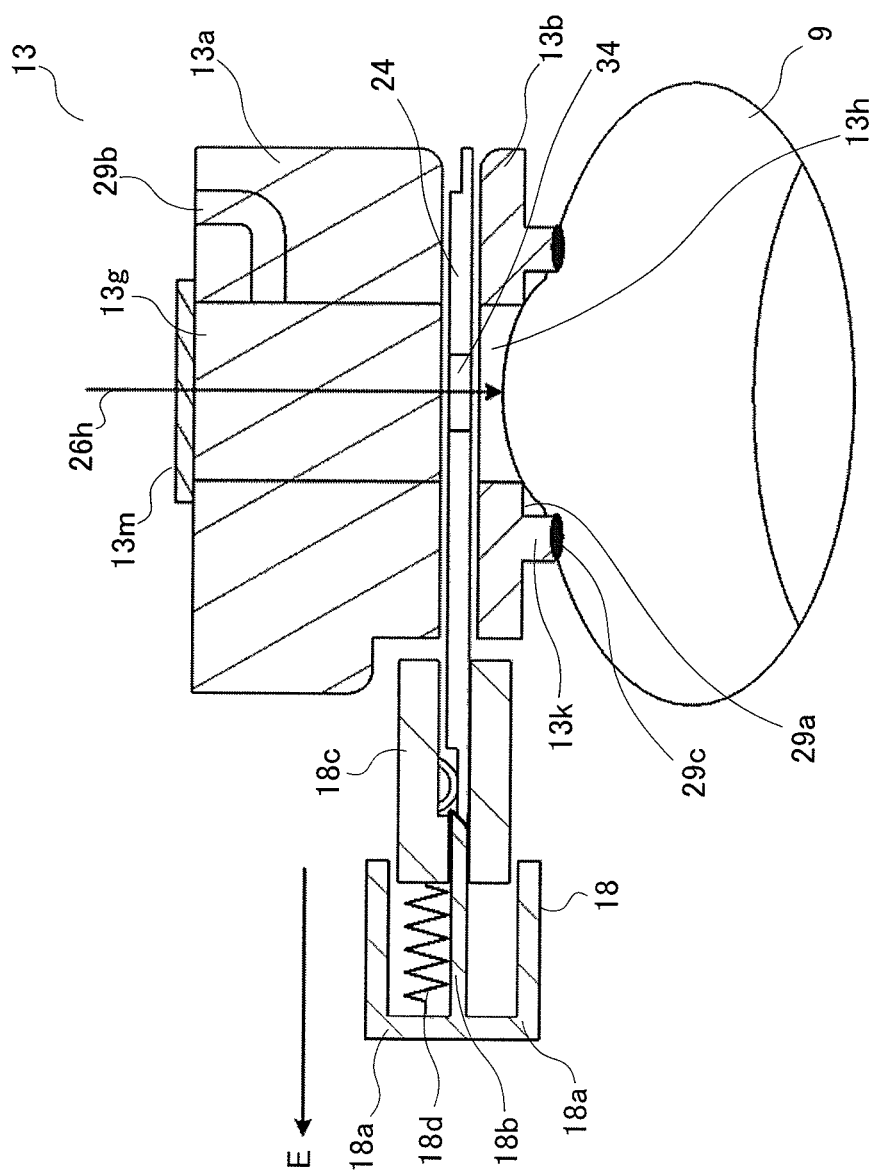
FIG. 15A is a cross sectional view showing when a puncturing section in the blood test apparatus according to Embodiment 1 punctures skin.

FIG. 15A is a cross sectional view showing puncturing section 13 at the time skin is punctured.

As shown in FIG. 15A, spring 18d is mounted so as to engage with ejection button 18a in connector 18 to bias ejection button 18a in the direction of arrow E. Pushing member 18b mounted in ejection button 18a contacts the neighborhood of connection electrodes 43a to 45a and 47a (see FIG. 17) formed in the leading edge side of sensor 24.

Upon puncturing, connection electrodes 43a to 45a and 47a formed in sensor 24 connect connector terminal 18c in connector 18. In addition, through-hole 13g penetrating upper holder 13a in the vertical direction, storing section 34 and through-hole 13h penetrating lower holder 13b in the vertical direction are arranged on a straight line, and laser light 26h emitted from laser puncturing unit 26 penetrates through-hole 13g and through-hole 13h to puncture skin 9.

Negative pressure path 29b introduces a negative pressure from negative pressure means 29 to negative pressure chamber 29a. Skin 9 is placed in a state of tension by applying a negative pressure to negative pressure chamber 29a, so that blood is easily sampled. Skin detecting sensor 29c is provided on bank 13k constituting negative pressure chamber 29a to detect contact with skin 9. In addition, transparent film 13m is removably provided on the top surface of through-hole 13g. Transparent film 13m is mounted in order to allow laser light 26h to pass through and not to attenuate laser light 26h due to adhesion of scattering materials to laser puncturing unit 26 at the time skin 9 is punctured. It is necessary to replace transparent film 13m on a regular basis at the time its transmittance is decreased. In addition, it is possible to improve the negative pressure performance by sealing hermetically through-hole 13g with transparent film 13m.

Upon puncturing, the user touches lower holder 13b with finger 9, lifts lower holder 13b until lower holder 13b contacts sensor 24 and applies a negative pressure using negative pressure means 29 to swell skin 9. In this state, puncturing is performed.

Connector 18 and sensor 24 are electrically connected to one another by inserting sensor 24 in connector 18 and contacting between connector terminal 18c and connection electrodes 41a to 45a (see FIG. 20) in sensor 24.

Sensor 24 is inserted in connector 18 and held in a cantilevered state.

The reason to sandwich sensor 24 between upper holder 13a and lower holder 13b is as follows. (1) To maintain the airtightness when a negative pressure is applied, and (2) to keep sensor 24 horizontal in order that laser light 26h is vertically incident on sensor 24.

Figure 15C:
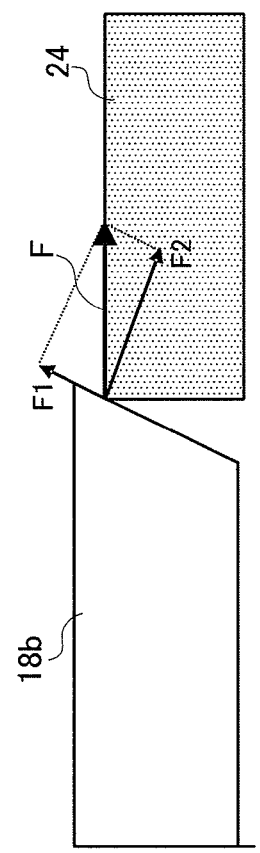
FIG. 15C is an enlarged view of primary parts of the pushing member in FIG. 15B.
Figure 15B:
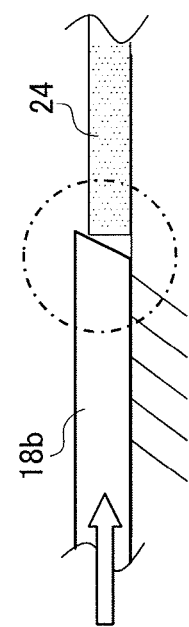
FIG. 15B is a drawing explaining the shape and operation of a pushing surface of a pushing member in the blood test apparatus according to Embodiment 1.

FIG. 15B is a drawing explaining the shape and operation of a pushing surface of the above-described pushing member 18b.

FIG. 15C is an enlarged view of primary parts of pushing member 18b in FIG. 15B.

As shown in FIG. 15B, pushing member 18b is a sliding mechanism and has an inclined part having a tapered surface to push out sensor 24.

As shown in FIG. 15C, the leading edge of pushing member 18b has an inclined plane toward the sensor rest surface. Force F from pushing member 18b is resolved into component F1 in the direction of this inclined plane and component F2 in the direction normal to the direction of the inclined plane, and pushing member 18b and sensor 24 move in the directions of component forces F1 and F2, respectively. Component force F2 moves sensor 24 in the direction to press down sensor 24 on the sensor rest surface.

By this configuration, it is possible to adequately press down sensor 24 when sensor 24 is ejected (pushed out) and is possible to reliably push out sensor 24 along the sensor rest surface of connector 18. Here, when it is not possible to reliably push out sensor 24, sensor 24 drops upon removing from the connector terminal, so that blood is likely to adhere to the lower holder by contact of the sensor with the lower holder. The present embodiment aims to prevent this drop of sensor 24 beforehand to improve further safety.

Figure 16:
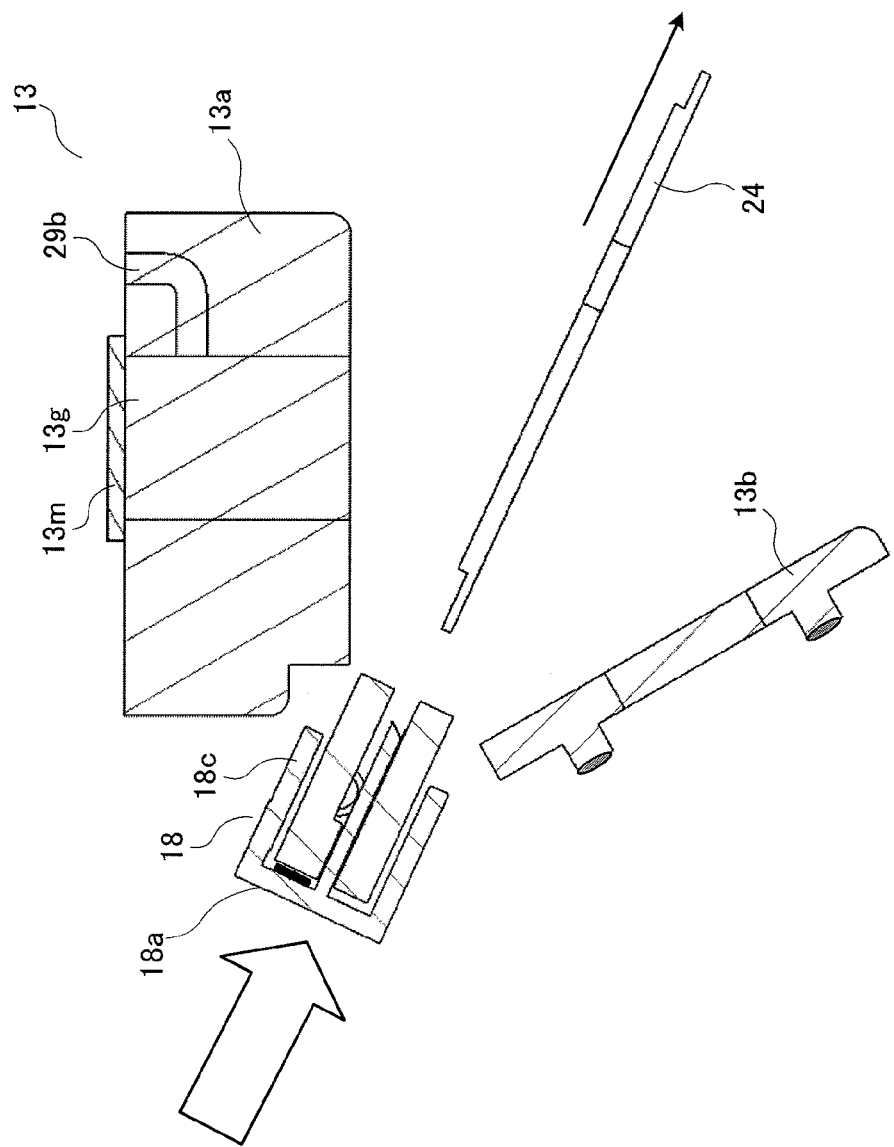
FIG. 16 is a cross sectional view showing when the puncturing section in the blood test apparatus according to Embodiment 1 ejects a sensor.

FIG. 16 is a cross sectional view when puncturing section 13 ejects a sensor.

As shown in FIG. 16, when puncturing and measurement are completed, the user rotates connector 18 and lower holder 13b by lifting ejection button 18a in connector 18.

At this time, lower holder 13b rotates at an angle equal to or greater than the angle of rotation of connector 18, so that sufficient spaces are created between upper holder 13a and sensor 24 and between lower holder 13b and sensor 24. Since there are sufficient spaces between sensor 24 and upper holder 13a and between sensor 24 and lower holder 13b, blood having adhered to sensor 24 does not adhere to the upper and lower holders.

As indicated by the arrow in FIG. 16, the user presses ejection button 18a in connector 18 to eject sensor 24.

As described above, after sensor 24 is discarded, the user lifts cover 16 in the apparatus body to touch the projecting part (not shown) provided in cover 16 (see FIG. 3) with lower holder 13b, so that lower holder 13b is pushed up. Lower holder 13b is lifted up to the position to be beyond projecting part 13d in upper holder 13a and returns to the state before sensor 24 is inserted.

Figure 17:
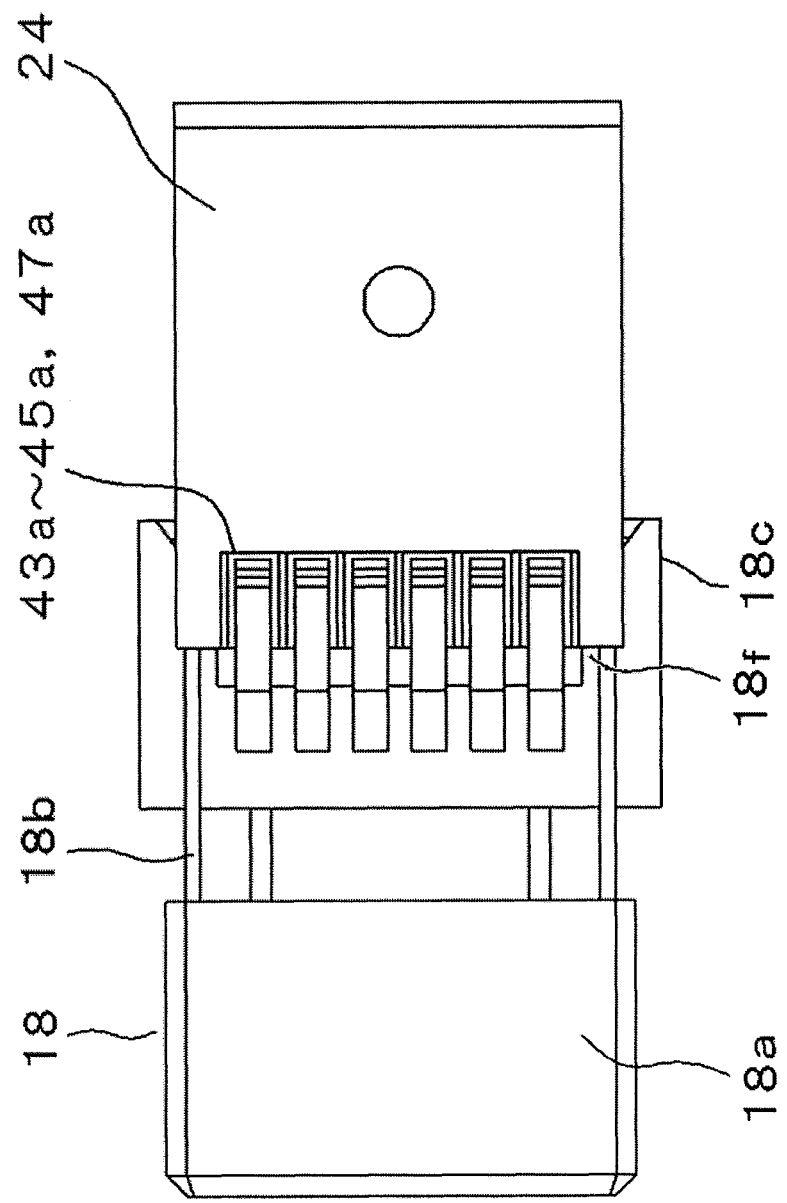
FIG. 17 is a transparent plan view showing a sensor mounted in the puncturing section in the blood test apparatus according to Embodiment 1 from above.
Figure 18:
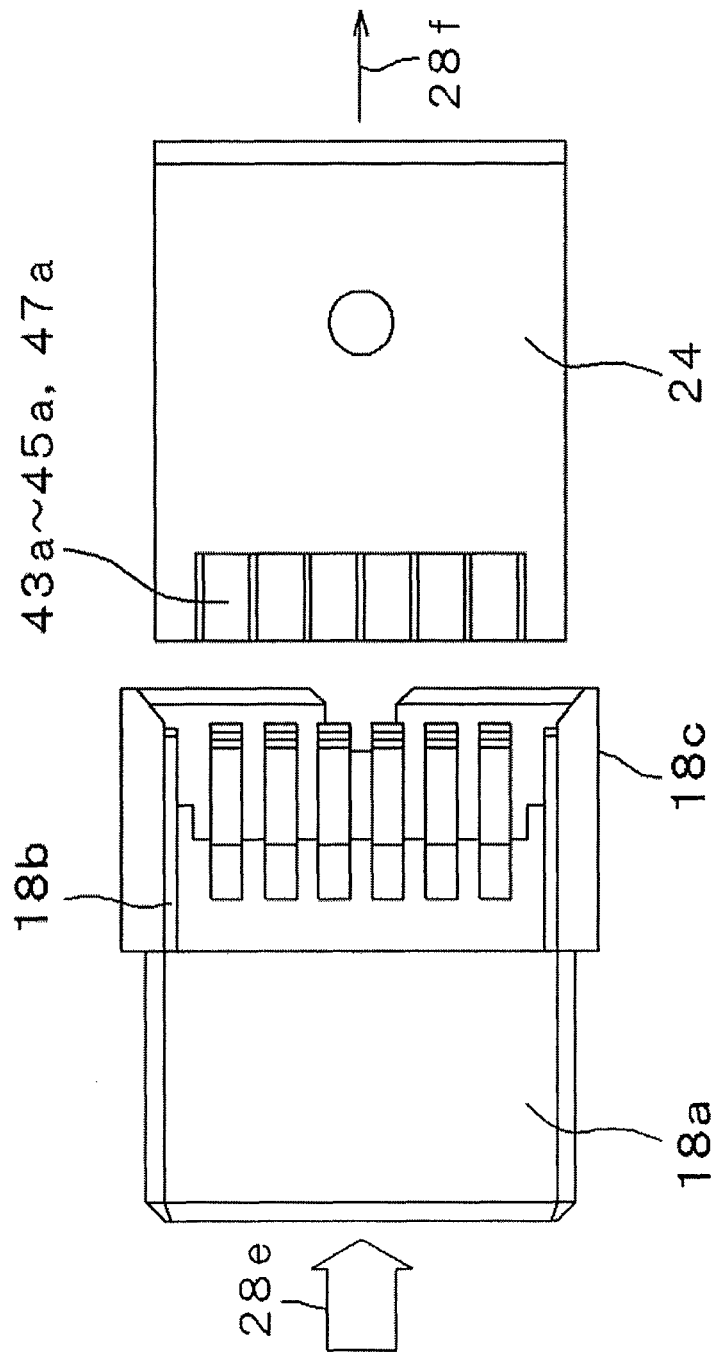
FIG. 18 is a transparent plan view showing when a sensor is ejected from the blood test apparatus according to Embodiment 1.

FIG. 17 is a transparent plan view showing sensor 24 mounted in puncturing section 13 from above. FIG. 18 is a transparent plan view when sensor 24 is ejected.

As shown in FIG. 17, connection electrodes 43a to 45a and 47a formed in the leading edge side of sensor 24 are connected with connector 18 by inserting sensor 24 in connector 18. At this time, the position of the leading edge side of sensor 24 is determined to contact concave part 18f in connector 18.

As shown in FIG. 18, the user pushes (presses) ejection button 18a in the direction of arrow 28e. Then, pushing member 25b (18b in the figure) pushes out sensor 24 in the direction of arrow 28f. Connection electrodes 43a to 45a and 47a in sensor 24 leave connector 18 in the lower holder, so that sensor 24 is ejected.

Figure 19:
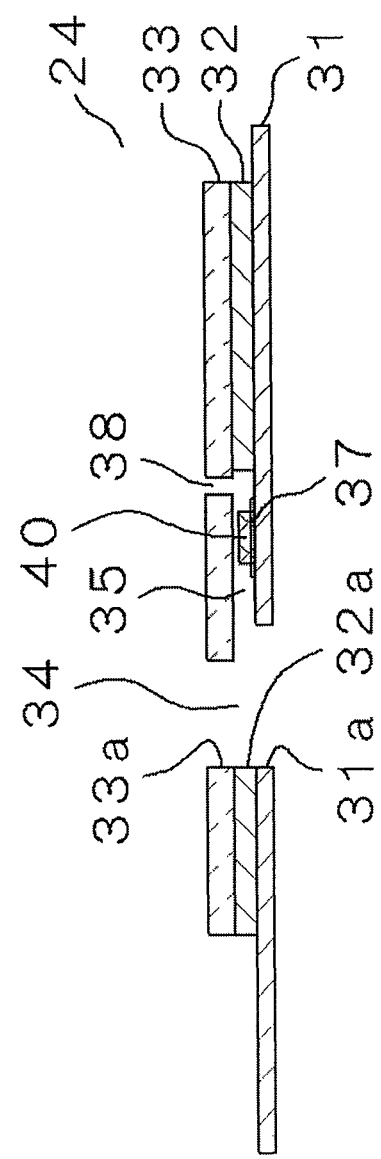
FIG. 19 is a cross sectional view of a sensor stored in a sensor cartridge in the blood test apparatus according to Embodiment 1.

FIG. 19 is a cross sectional view showing a sensor stored in a sensor cartridge.

As shown in FIG. 19, sensor 24 is composed of substrate 31, spacer 32 pasted on the top surface of substrate 31 and cover 33 pasted on the top surface of spacer 32.

Storing section 34 temporarily stores blood. Storing section 34 is formed by connecting substrate hole 31a formed at approximately the center of substrate 31, spacer hole 32a formed in spacer 32 corresponding to substrate hole 31a and cover hole 33a formed in cover 33 corresponding to substrate hole 31a to communicate with each other.

One end of supply path 35 is coupled to storing section 34 and introduces blood stored in storing section 34 to detecting section 37 at a breath by capillary action. The other end of supply path 35 is coupled to air hole 38. The capacity of storing section 34 is 0.904 µL and the capacity of supply path 35 is 0.44 µL. As described above, the test can be performed using a small amount of blood 10, and therefore, the burden of the patient is reduced.

Reagent 40 placed on detecting section 37 is formed by adding and dissolving PQQ-GDH (0.1 to 5.0 U/sensor), potassium ferricyanide (10 to 200 millimoles), maltitol (1 to 50 millimoles) and taurine (20 to 200 millimoles) in a CMC solution of 0.01 to 2.0 wt % to prepare a reagent solution, by dropping the reagent solution on detection electrodes 41 and 43 (see FIG. 20) formed on substrate 31 and drying. When reagent 40 absorbs moisture, deterioration of the performance of reagent 40 is advanced. In order to prevent this deterioration, desiccant 27 is accommodated in sensor cartridge 27.

An electrically conductive layer is formed on the top surface of substrate 31 by the sputtering method or the vapor deposition method using materials such as gold, platinum, or palladium. Detection electrodes 41 to 45 (see FIG. 20), connection electrodes 41a to 45a derived from these detection electrodes 41 to 45 and identification electrode 47a are integrally formed by applying laser machining to the electrically conductive layer.

In addition, the same material, polyethylene terephthalate (PET), is used for substrate 31, spacer 32 and cover 33. By using the same material, the cost can be reduced.

Figure 20:
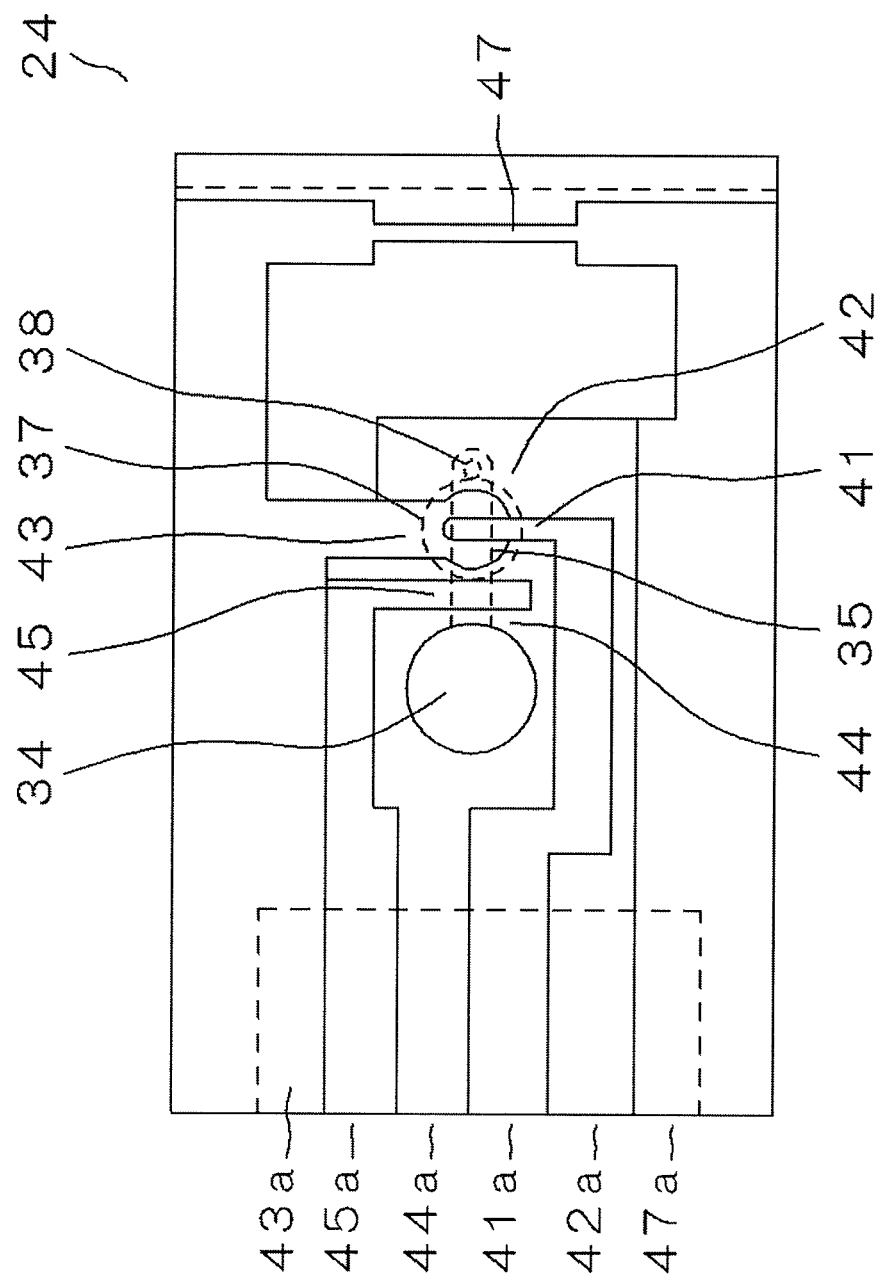
FIG. 20 is a transparent plan view of a sensor for the blood test apparatus according to Embodiment 1.

FIG. 20 is a transparent plan view of sensor 24 having a rectangular shape.

As shown in FIG. 20, connection electrodes 41a to 45a respectively derived from detecting electrodes 41 to 45 and identification electrode 47a are formed in one end of sensor 24. Identifying section 47, which has a conductor pattern, is formed between connection electrode 43a and identification electrode 47a.

Storing section 34 is provided in approximately the center of sensor 24, and supply path 35 having one end connected to storing section 34 is provided toward detection electrode 42. The other end of supply path 35 is coupled to air hole 38.

Storing section 34, detection electrode 44 connected to connection electrode 44a, detection electrode 45 connected to connection electrode 45a, again detection electrode 44 connected to connection electrode 44a, detection electrode 43 connected to connection electrode 43a, detection electrode 41 connected to connection electrode 41a, again detection electrode 43 connected to connection electrode 43a and detection electrode 42 connected to connection electrode 42a, are provided on supply path 35, in the order described. In addition, reagent 40 (see FIG. 19) is placed on detection electrodes 41 and 43.

It is possible to identify whether sensor 24 is mounted in puncturing section 13 based on whether there is electrical conduction between connection electrode 43a and identification electrode 47a. That is, when sensor 24 is conveyed to puncturing section 13, the electrical conduction between connection electrode 43a and identification electrode 47a is detected, so that it is possible to detect whether sensor 24 is mounted reliably in puncturing section 13. If there is no electrical conduction, sensor 24 is not mounted in puncturing section 13. In this case, it is possible to display a warning indication on display section 50 (see FIG. 22) of blood test apparatus 11.

In addition, storage of information about the calibration curve to be used or storage of manufacturing information is allowed by changing the electrical resistance of identifying section 47. It is possible to perform blood test more accurately by using those information.

Figure 21:
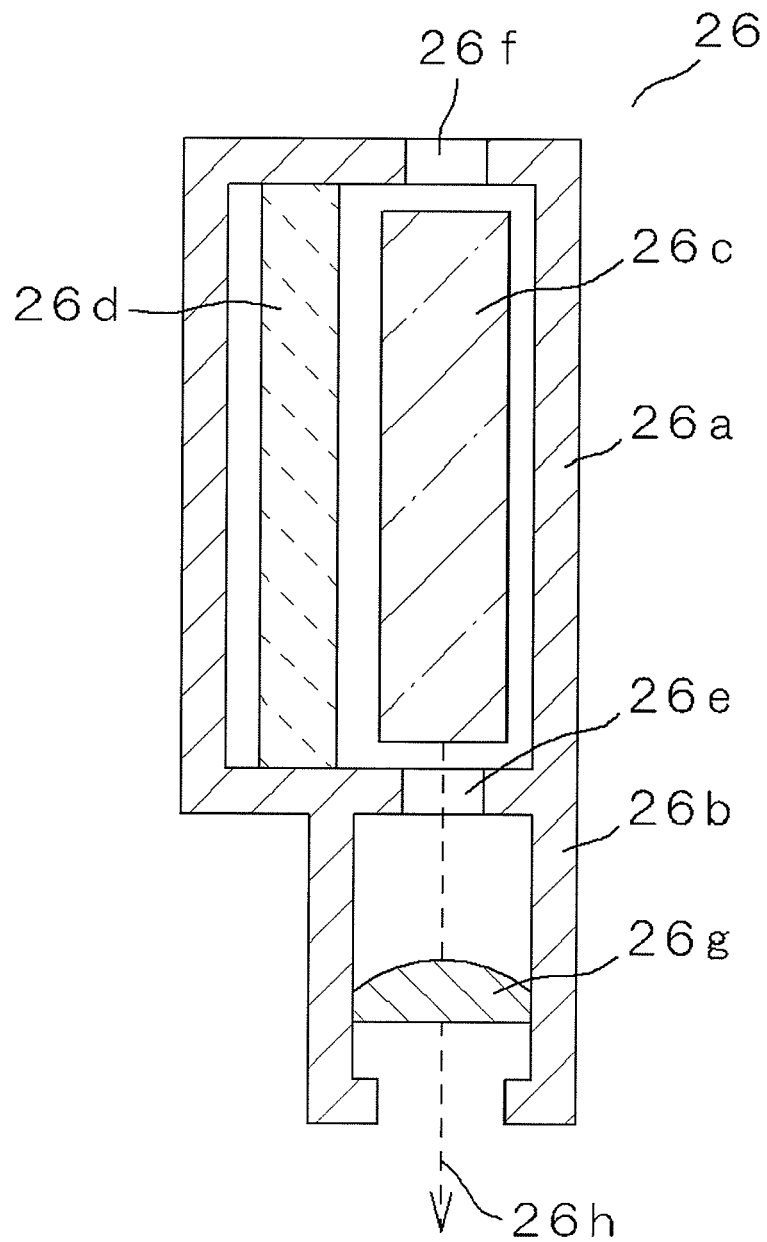
FIG. 21 is a cross sectional view of a laser puncturing unit in the blood test apparatus according to Embodiment 1.

FIG. 21 is a cross sectional view of laser puncturing unit 26.

As shown in FIG. 21, laser puncturing unit 26 is composed of oscillating tube 26a and cylindrical body 26b coupled to this oscillating tube 26a. Er:YAG (yttrium, aluminium, garnet) laser crystal 26c and flash light source 26d (shown as an example of excitation light source) are housed in oscillating tube 26a. Partially transmitting mirror 26e having a transmittance of about 1% is mounted in one end of oscillating tube 26a, and total reflecting mirror 26f is mounted in the other end of oscillating tube 26a. Convex lens 26g is mounted in cylindrical body 26b beyond partially transmitting mirror 26e and is set to focus laser light 26h under the skin of the patient.

Now, operations of the above-described laser puncturing unit 26 will be explained.

Figure 22:
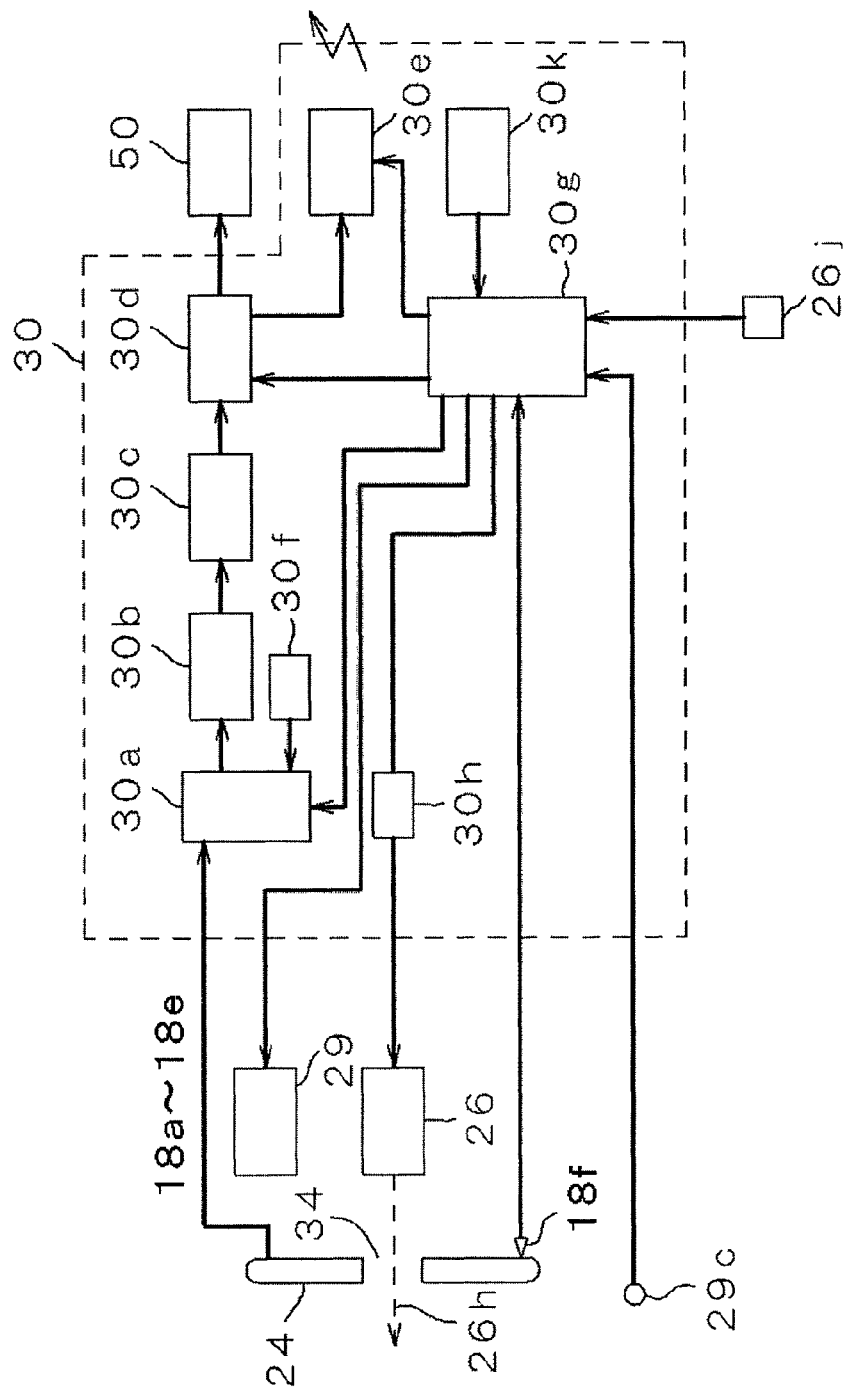
FIG. 22 is a block diagram showing an electrical circuit section and its neighborhood in the blood test apparatus according to Embodiment 1.

The user presses puncturing button 26j (see FIG. 22). Then, flash light source 26d emits light. The light emitted from flash light source 26d enters Er:YAG laser crystal 26c, and, here, reflects and resonates between total reflection mirror 26f, Er:YAG laser crystal 26c and partially transmitting mirror 26e and is amplified. Part of the amplified laser light passes through partially transmitting mirror 26e by stimulated emission. Laser light 26h passing through partially transmitting mirror 26e is emitted through lens 26g and focuses on under skin 9. The appropriate focal depth for puncturing is 0.1 mm to 3 mm from skin 9.

The present embodiment employs laser puncturing unit 26 that is able to puncture skin 9 of the patient in a noncontact state and therefore provides sanitation. In addition, laser puncturing unit 26 has no moving components, and therefore, is less susceptible to breakdown.

FIG. 22 is a block diagram showing electrical circuit section 30 and its neighborhood.

As shown in FIG. 22, electrical circuit section 30 is configured to include switching circuit 30a, current/voltage convertor 30b, analog/digital convertor (hereinafter "A/D convertor") 30c, computing section 30d, transmitting section 30e, reference voltage source 30f, timer 30k, high-voltage generating circuit 30h and control section 30g.

Connection electrodes 41a to 45a (see FIG. 20) in sensor 24 are connected to switching circuit 30a through connectors 18a to 18e.

Switching circuit 30a receives, at its control terminal, commands from control section 30g and switches between the output voltage from connectors 18a to 18e, to which connection electrodes 41a and 45a are connected, and the reference voltage from reference voltage source 30f. This reference voltage source 30f may be the ground potential.

Current/voltage convertor 30b is configured by an operational amplifier and so forth, and converts the detected signal outputted from switching circuit 30a to a voltage.

A/D convertor 30c converts the detected signal outputted from current/voltage convertor 30b to a digital signal and outputs the digital signal to computing section 30d.

Computing section 30d performs computation for blood analysis by referring to fixed data and table values stored inside, based on the detected signal converted to a digital signal, according to a command from control section 30g. Computing section 30d outputs the result of measurement and analysis to display section 50 and transmitting section 30e.

Transmitting section 30e has an I/O interface section and outputs the result of measurement and analysis to the outside according to a command from control section 30g.

Timer 30k measures time for various timings including a puncturing timing, a driving timing of negative pressure means 29, a skin detection timing and so forth.

High-voltage generating circuit 30h generates a high voltage to drive laser puncturing unit 26 according to a command from control section 30g.

Control section 30g is configured by a microcomputer and so forth, and controls entire blood test apparatus 11. Control section 30g receives, as input, signals from puncturing button 26j that allows laser light 26h to be emitted, a skin detected signal from skin detecting sensor 29c and a time measurement signal from timer 30k. Control section 30g performs blood test (described later with FIG. 23) based on each of the above-described input signals.

Next, operations of electrical circuit section 30 will be explained.

First, the user presses puncturing button 26j to puncture skin 9 with laser puncturing unit 26. The properties of blood exuding by puncturing are measured. In a measurement operation, control section 30g switches switching circuit 30a and connects detection electrode 41 to current/voltage convertor 30b. In addition, control section 30g connects detection electrode 42, which is a detecting electrode to detect blood flowing in, to reference voltage source 30f. Then, control section 30g applies a certain voltage between detection electrode 41 and detection electrode 42. In this state, when blood flows in, a current flows between detection electrodes 41 and 42. This current is converted to a voltage by current/voltage convertor 30b and its voltage value is converted to a digital value by A/D convertor 30c. Then, the digital value is outputted to computing section 30d. Computing section 30d detects that blood has sufficiently flowed in based on the above-described digital value. Here, at this time, the operation of negative pressure means 29 is turned off.

Next, glucose, a blood component, will be measured. To measure the glucose level, first, control section 30g gives a command to switch switching circuit 30a and connects detection electrode 41 serving as a working electrode for measuring the glucose level, to current/voltage convertor 30b. In addition, control section 30g connects detection electrode 43 serving as a counter electrode for measuring the glucose level, to reference voltage source 30f.

Here, for example, while the glucose in blood and its oxidation-reduction enzyme react for a given period of time, control section 30g turns off current/voltage convertor 30b and reference voltage source 30f. Then, after a certain period of time (1 to 10 seconds) has passed, control section 30g gives a command to apply a certain voltage (0.2 to 0.5 V) between detection electrodes 41 and 43. By this means, a current flows between detection electrodes 41 and 43. This current is converted into a voltage by current/voltage convertor 30b, and its voltage value is converted into a digital value by A/D convertor 30c. Then, this digital value is outputted to computing section 30d. Computing section 30d calculates the glucose level based on this digital value.

After the glucose level is measured, the Hct value is measured. The Hct value is measured as follows. First, control section 30g gives a command to switch switching circuit 30a. Then, control section 30g connects detection electrode 45 serving as a working electrode for measuring the Hct value, to current/voltage convertor 30b. In addition, control section 30g connects detection electrode 41 serving as a counter electrode for measuring the Hct value, to reference voltage source 30f.

Next, control section 30g gives a command to current/voltage convertor 30b and reference voltage source 30f to apply a certain voltage (2 V to 3 V) between detection electrodes 45 and 41. The current flowing between detection electrodes 45 and 41 is converted into a voltage by current/voltage convertor 30b, and its voltage value is converted into a digital value by A/D convertor 30c. Then, this digital value is outputted to computing section 30d. Computing section 30d calculates the Hct value based on this digital value.

With reference to a calibration curve or calibration curve table determined in advance, computing section 30d corrects the glucose level with the Hct value using the Hct value and the glucose level resulting from this measurement, and displays the corrected result on display section 150. Control section 30g determines which calibration curve or calibration curve table is used according to identifying section 47 in sensor 24. In addition, control section 30g controls to transmit the result corrected using the calibration curve or calibration curve table from transmitting section 30e to an injection device to inject insulin and to receive, at transmitting section 30e, the result from other information equipment. Although a radio wave may be used for this communication, communication is preferably performed by optical communication that does not interfere with medical equipment.

As described above, by adopting the configuration in which the dose of insulin to administer is automatically set by transmitting corrected measurement data from transmitting section 30e, it is not necessary to set the dose of insulin to be administered by the patient, so that there is no trouble with setting. Moreover, it is possible to set the dose of insulin in an injection device without human work, so that it is possible to prevent mistakes in setting.

Although measurement of glucose levels has been explained as an example, the present invention is applicable to measurement of levels of blood components such as lactic acid and cholesterol other than glucose by changing reagent 40 in sensor 24.

Next, a test method using blood test apparatus 11 will be explained.

Figure 23:
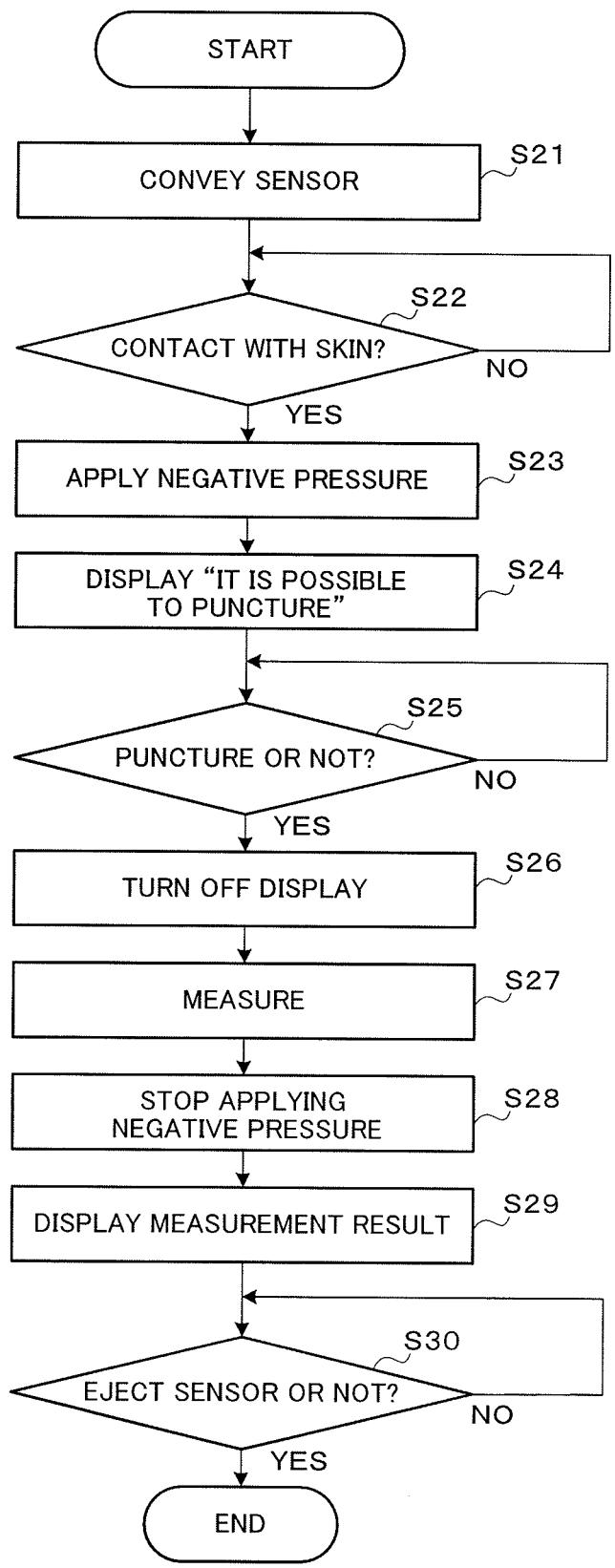
FIG. 23 is a flowchart of a blood test method using the blood test apparatus according to Embodiment 1.

FIG. 23 is a flowchart of a blood test method using blood test apparatus 11. S represents each step in the figure.

First, in step S21, slide plate 27g (see FIG. 4) constituting conveying section 27d (see FIG. 4) conveys sensor 24 (see FIG. 4) to puncturing section 13 (see FIG. 4) and inserts connection electrodes (41a to 45a and 47a) in sensor 24 in connector 18. Confirmation of this conveyance is performed by detecting electrical conduction between connection electrode 43a (see FIG. 20) and identification electrode 47a (see FIG. 20) in sensor 24. Then, slide plate 27g is returned to a standby state by spring 27h (see FIG. 4) constituting conveying section 27d.

In step S22, control section 30g checks that puncturing section 13 contacts skin 9 of the patient based on a detected signal from skin detecting sensor 29c. In order to do this, control section 30g displays an indication to prompt contact with skin 9 on display section 50. The patient contacts puncturing section 13 with skin 9 of the patient following this indication.

When the contact with skin 9 is confirmed, control section 30g operates negative pressure means 29 to apply a negative pressure to negative pressure chamber 29a provided in puncturing section 13 in step S23. Skin 9 swells by applying a negative pressure. In addition, upon detecting an output from skin detecting sensor 29c, control section 30g operates high-voltage generating circuit 30h to start charging a capacitor at a high voltage.

When the current varies resulting from the operation of negative pressure means 29, when high-voltage generating circuit 30h finishes charging at a high voltage or when timer 30k measures a predetermined period of time, control section 30g determines that the high voltage enough for puncturing has been charged and skin 9 in storing section 34 has swelled sufficiently, and the step moves to step S24.

In step S24, control section 30g displays an indication that "it is possible to puncture skin 9" on display 50.

In step S25, control section 30g waits for puncturing button 26j to be pressed. When puncturing button 26j is pressed, the step moves to step S26.

Here, it is possible to automate the above-described operation to press puncturing button 26j in step S25 based on the indication that "it is possible to puncture skin 9".

In step S26, control section 30g turns off the display in step S24.

In step S27, blood exuding by puncturing skin 9 is taken into storing section 34 in sensor 24. Blood 10 taken into storing section 34 is taken into detecting section 37 at a breath (at a fixed flow rate) by the capillary action of supply path 35. Control section 30g measures the blood sugar level of blood.

In step S28, control section 30g turns off negative pressure means 29.

In step S29, control section 30g displays the measured blood sugar level on display section 50. Here, negative pressure means 29 may be turned off at the time blood 10 arrives at detection electrode 42.

Now, measurement of blood ends and the step moves to step S30.

In step S30, sensor 24 is ejected out of blood test apparatus 11 by pressing ejection button 25a.

In this step S30, lower holder 13b and connector 18 are rotated to form spaces between upper holder 13a and sensor 24 and between lower holder 13b and sensor 24, respectively.

In this state, sensor 24 is ejected, so that it is possible to eject sensor 24 without allowing contact of blood having adhered to sensor 24 with puncturing section 13, cartridge 27 and so forth. Therefore, puncturing section 13 is not stained with blood having adhered to sensor 24, puncturing section 13 and its neighborhood are kept clean.

In addition, sensor 24 is automatically ejected by pressing ejection button 25a in the direction opposite to the finger pressing ejection button 25a, so that it is possible to discard used sensor 24 without allowing contact of used sensor 24 with a finger and so forth. It is possible to keep the finger clean without being stained with blood.

Moreover, sensor 24 is ejected back to the sensor inserting inlet 13c to insert sensor 24. Here, connector terminal 18c in connector 18 provided in the leading edge side of sensor 24 contacts only substrate 31 in sensor 24 and does not ride on spacer 32 and cover 33. Therefore, the burden on connector 18c is reduced, so that it is possible to extend the durability of insertion and extraction of connector 18.

As described above, according to the present embodiment, blood test apparatus 11 includes puncturing section 13 composed of upper holder 13a and lower holder 13b and connector 18, and, when puncturing is performed, connector 18, upper holder 13a and lower holder 13b sandwich and hold sensor 24, and when sensor 24 is ejected, lower holder 13b is rotated to part from upper holder 13a and this rotation forms a space between lower holder 13b and upper holder 13a to expose sensor 24. Therefore, it is possible to eject sensor 24 without allowing contact of blood and so forth having adhered to sensor 24 with puncturing section 13, so that it is possible to keep the interior of the apparatus including puncturing section 13 clean.

In addition, since sensor 24 is ejected in a sufficient space, sensor 24 is easily discarded. Moreover, it is possible to discard sensor 24 without touching used sensor 24 with fingers, and therefore, fingers are not stained with blood and kept clean, and sanitation and safety are provided.

With the present embodiment, in particular, connector 18 and lower holder 13b are separately provided, and, when a sensor is ejected (discarded), lower holder 13b is opened by the rotation of connector 18 at an angle greater than the angle of rotation of connector 18, so that it is possible to increasingly improve the effect of preventing puncturing section 13 and so forth from being stained.

Here, with the present embodiment, although an example has been explained where skin is punctured by penetrating sensor 24 held by puncturing section 13 from the upper holder 13a side, the puncturing position and the structure of sensor 24 are not limited as far as the apparatus has a mechanism to rotate lower holder 13b to part from upper holder 13a when the sensor is ejected. For example, the present invention is applicable to not only a model to perform puncturing by penetrating a sensor but also a model to dispense blood as drops to the end part of a sensor, and allows the same effect.

Moreover, although the present embodiment adopts a configuration in which upper holder 13a is mounted on an end surface of housing 12 and lower holder 13b is mounted in a corner of housing 12 to provide excellent operability, these positions to provide upper holder 13a and lower holder 13b are merely examples and are by no means limiting. Likewise, rotating shaft 19 may be provided in either the housing 12 side or the upper holder 13a side, or two rotating shafts may be provided.

Embodiment 2

With Embodiment 1, a configuration has been explained where puncturing section 13 composed of upper holder 13a and lower holder 13b is provided. Upper holder 13a has a function to make airtight not to let out a negative pressure, in addition to a function to sandwich and hold sensor 24 between lower holder 13b and upper holder 13a. Therefore, when the present embodiment is applied to a blood test apparatus not using a negative pressure, upper holder 13a is not necessarily required.

With Embodiment 2, blood test apparatus 11A having a sensor holding section and a holder (finger holding section) will be explained.

Figure 24:
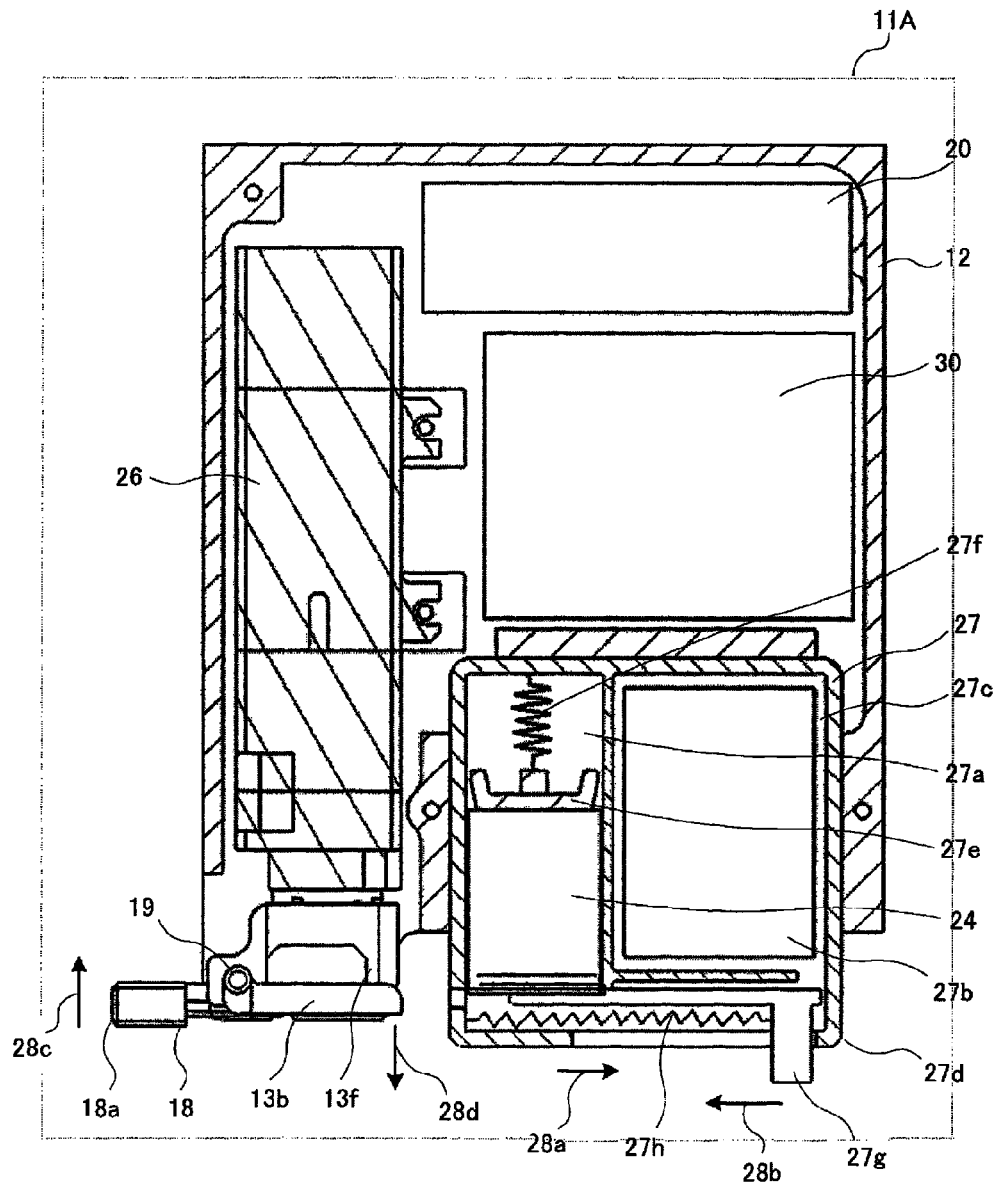
FIG. 24 is a cross sectional view showing a blood test apparatus according to Embodiment 2 of the present invention when a cover is removed.
Figure 25:
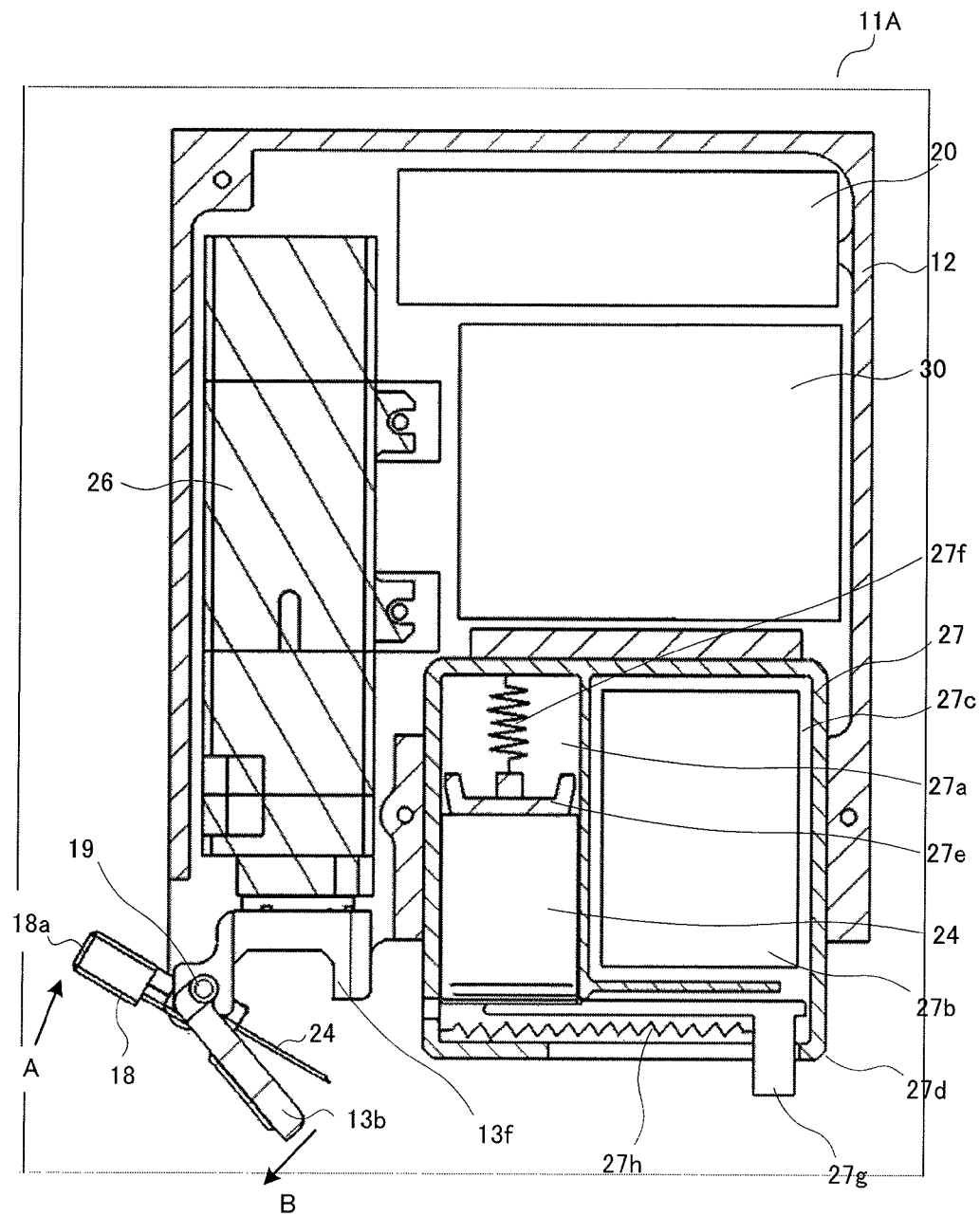
FIG. 25 is a cross sectional view showing when a sensor is ejected from the blood test apparatus according to Embodiment 2.

FIG. 24 is a cross sectional view of blood test apparatus 11A when cover 16 is removed according to Embodiment 2 of the present invention. FIG. 25 is a cross sectional view of blood test apparatus 11A when a sensor is ejected. FIG. 24 and FIG. 25 correspond to FIG. 4 and FIG. 5, respectively. The same components as in FIG. 24 and FIG. 25 will be assigned the same reference numerals and overlapping descriptions will be omitted.

As shown in FIG. 24 and FIG. 25, blood test apparatus 11A has lower holder 13b and stopper 13f that places lower holder 13b in a predetermined position instead of puncturing section 13 composed of upper holder 13a and lower holder 13b shown in FIG. 4 and FIG. 5.

Blood test apparatus 11A does not use a negative pressure, and therefore, it is possible to eliminate upper holder 13a (see FIG. 4). When a negative pressure is used, upper holder 13a is required to secure airtightness between the puncturing apparatus and sensor 24.

Since upper holder 13a is eliminated, the number of holders is one, so that it is possible to refer to lower holder 13b simply as "holder 13b." Here, when lower holder 13b is pushed up in measurement, stopper 13f is required to place lower holder 13b in a predetermined position.

As shown in FIG. 25, lower holder 13b rotates at an angle approximately twice as large as the angle to eject sensor 24 and is opened widely from stopper 13f. Large spaces are formed above the top surface and below the bottom surface of sensor 24, so that, in addition to an effect of easily ejecting (discarding) sensor 24, adhesion of blood to lower holder 13b is effectively prevented.

As described above, according to the present embodiment, even if blood test apparatus 11A does not use a negative pressure, it is possible to provide the same effect as Embodiment 1, that is, it is possible to eject sensor 24 without allowing contact of blood and so forth having adhered to sensor 24 with lower holder 13b, so that it is possible to keep the interior of the apparatus including lower holder 13b clean.

Embodiment 3

With Embodiments 1 and 2, blood test apparatus 11 including a sensor cartridge has been explained. With Embodiment 3, blood test apparatus 11B without a sensor cartridge will be explained.

Figure 26:
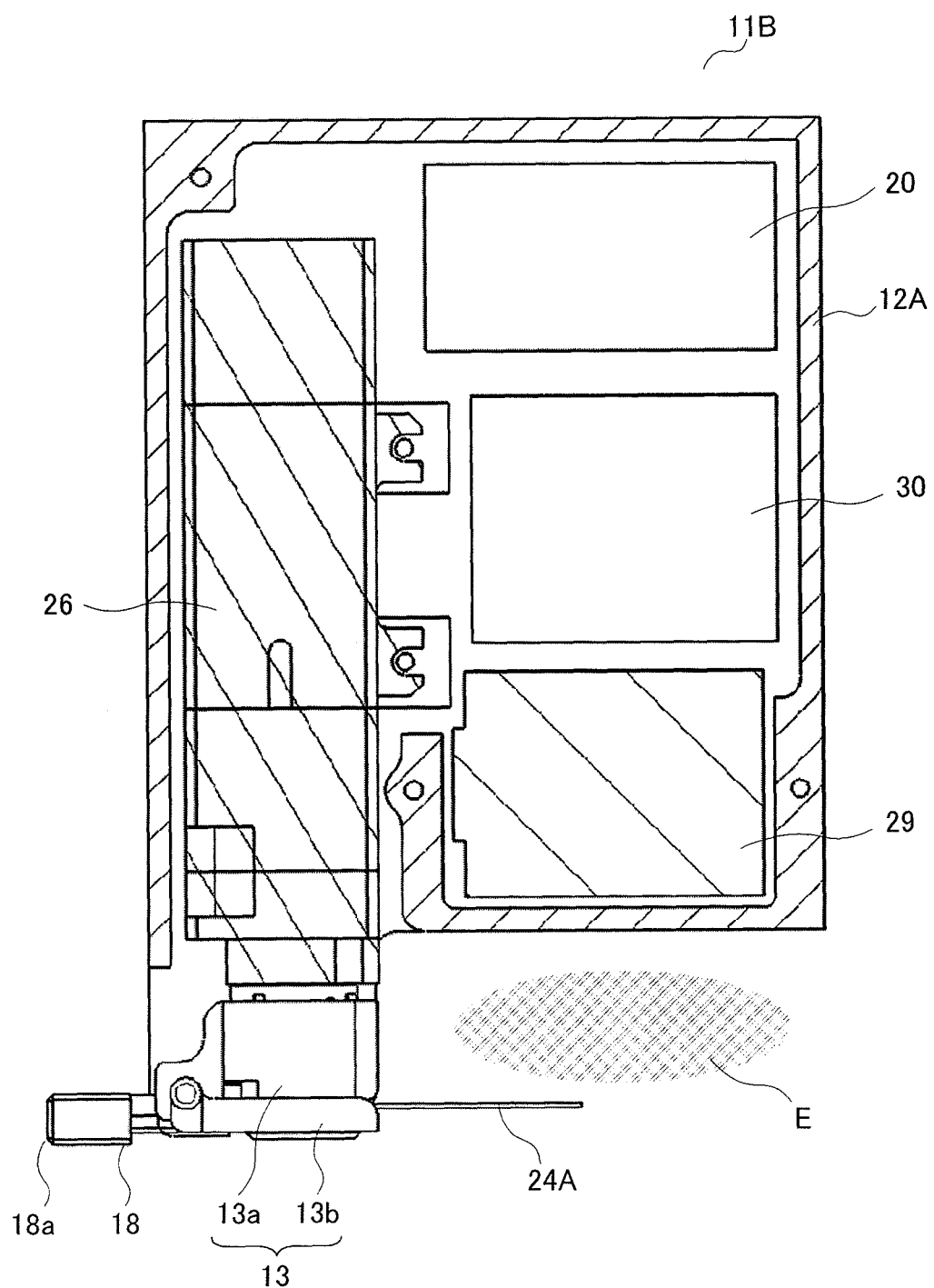
FIG. 26 is a cross sectional view of a blood test apparatus according to Embodiment 3 of the present invention without a sensor cartridge.

FIG. 26 is a cross sectional view of blood test apparatus 11B without a sensor cartridge according to Embodiment 3 of the present invention. Blood test apparatus 11B according to the present embodiment is the same as blood test apparatus 11 according to Embodiment 1 except that the configuration without a sensor cartridge is adopted. The same components as in FIG. 4 will be assigned the same reference numerals and overlapping descriptions will be omitted.

As shown in FIG. 26, blood test apparatus 11B has puncturing section 13 in a lower corner of housing 12A. Puncturing section 13 is composed of upper holder 13a, lower holder 13b and connector 18, and sandwiches and fixes sensor 24A between upper holder 13a and lower holder 13b.

Since sensor 24A is inserted in connector 18 by pinching with fingers, sensor 24A is longer than sensor 24 according to Embodiment 1 by the length to pinch with fingers.

In addition, blood test apparatus 11B is provided with space E to insert fingers in order to insert (discard) a sensor.

Figure 27:
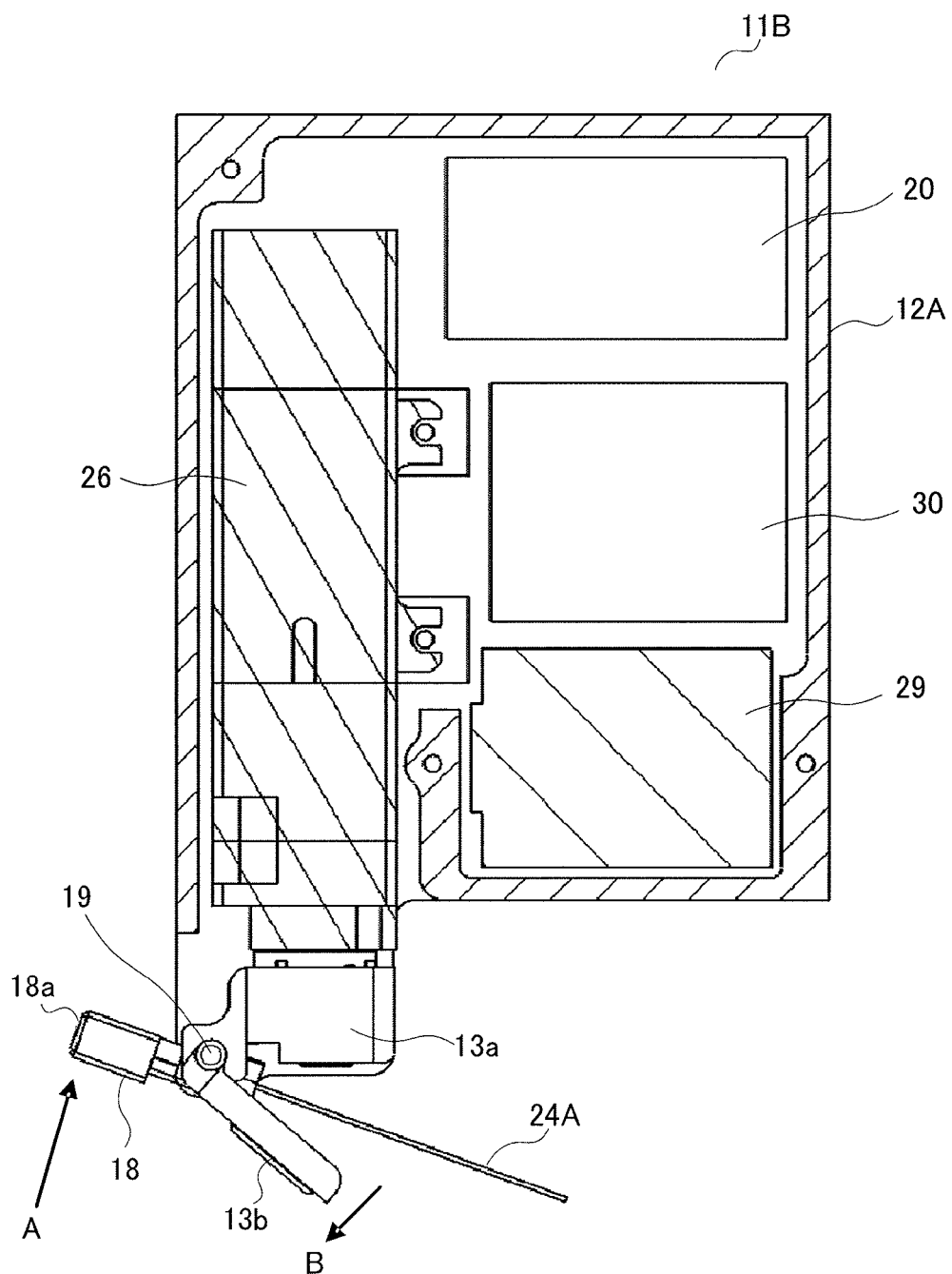
FIG. 27 is a cross sectional view showing when a sensor is ejected from the blood test apparatus according to Embodiment 3.
Figure 28:
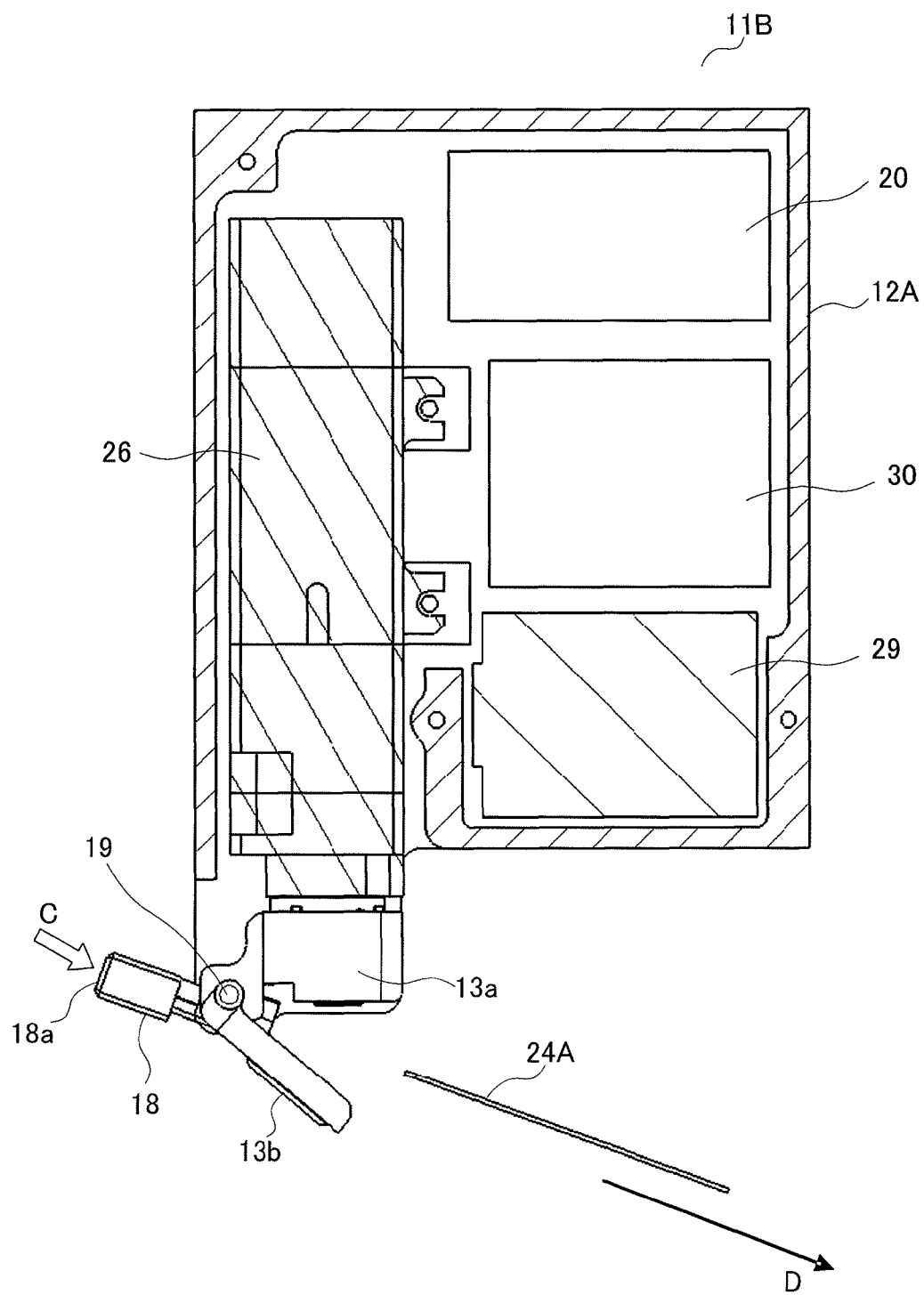
FIG. 28 is a cross sectional view showing when a sensor is ejected from the blood test apparatus according to Embodiment 3.

FIG. 27 and FIG. 28 are cross sectional views of blood test apparatus 11B when a sensor is ejected. FIG. 27 shows a second state and FIG. 28 shows a third state. FIG. 27 and FIG. 28 correspond to FIG. 5 and FIG. 6, respectively.

Blood test apparatus 11B performs the same sensor ejecting (discarding) operation as "[sensor ejecting (discarding) operation 1] and "[sensor ejecting (discarding) operation 2] described with reference to FIG. 5 and FIG. 6.

Figure 29:
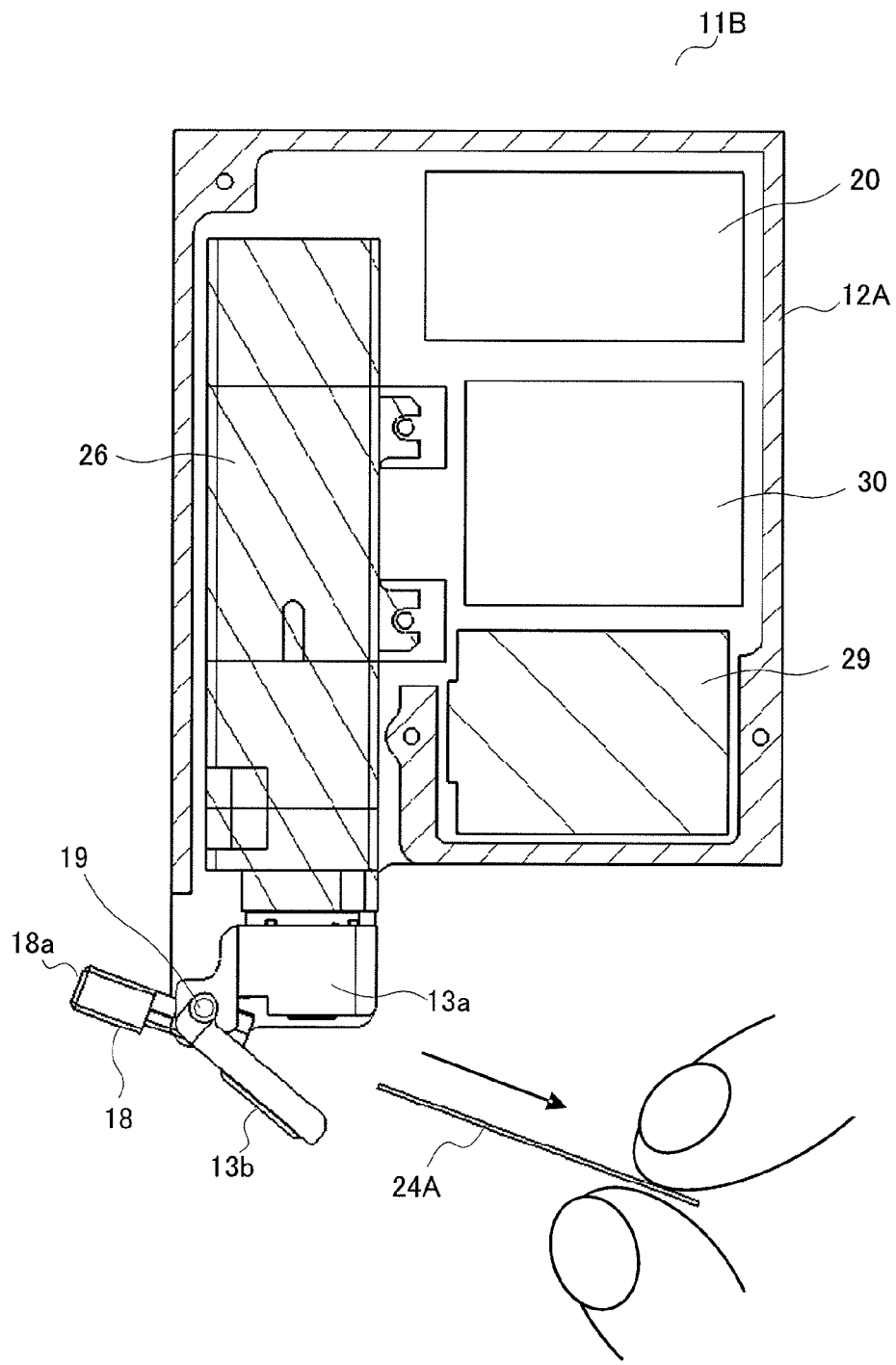
FIG. 29 is a cross sectional view showing when a sensor is ejected from the blood test apparatus according to Embodiment 3.

FIG. 29 is a cross sectional view of blood test apparatus 11B showing a state when a sensor is ejected (discarded), and shows a method of ejecting sensor 24A by sandwiching sensor 24A between fingers.

As shown in FIG. 29, blood test apparatus 11B has long sensor 24A by the length for handle, so that it is possible to bring out sensor 24A by directly pinching sensor 24 with fingers without using ejection button 18a (sensor pushing function). Therefore, a configuration in which ejection button 18a in connector 18 is omitted or shortened is possible. By the above-described configuration, it is possible to reduce the projecting part from housing 12A, so that it is possible to further reduce the size of housing 12A in blood test apparatus 11B.

Embodiment 4

With Embodiments 1 and 3, lower holder 13b and connector 18 are provided as separate parts. Embodiments 4 to 6 shows examples in which lower holder 13b and a connector are formed integrally.

Figure 30:
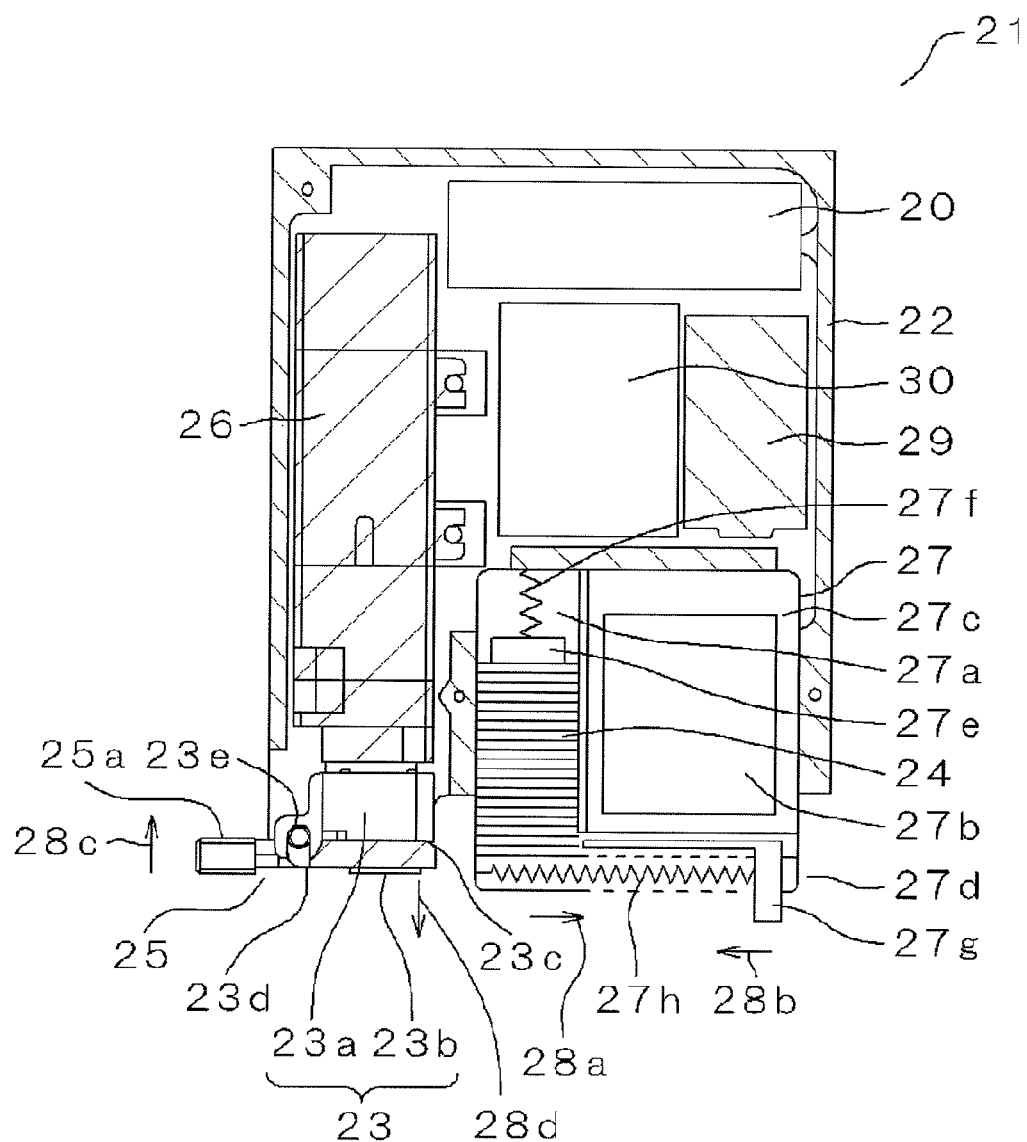
FIG. 30 is a cross sectional view of a blood test apparatus according to Embodiment 4 of the present invention.

FIG. 30 is a cross sectional view of a blood test apparatus according to Embodiment 4 of the present invention. The same components as in FIG. 4 will be assigned the same reference numerals and overlapping descriptions will be omitted.

As shown in FIG. 30, blood test apparatus 21 has housing 22 made of resin and having an approximately rectangular solid shape. Puncturing section 23 is mounted in a lower corner of housing 22. Puncturing section 23 is composed of upper holder 23a and lower holder 23b, and sandwiches and fixes sensor 24 between upper holder 23a and lower holder 23b.

Lower holder 23b is provided with supporting point 23e in the neighborhood of end 23d up to which sensor 24 is inserted, and formed to be able to rotate downward (the direction of arrow 28d) about supporting point 23e.

Ejection button 25a constituting ejecting means 25 is slidably coupled to the neighborhood of end 23d up to which lower holder 23b is inserted. By rotating ejection button 25a upward (the direction of arrow 28c), the sensor insertion inlet 23c side, which is the sensor cartridge 27 side of lower holder 23b, rotates downward.

Laser puncturing unit 26 (used as an example of a puncturing means) is mounted to face puncturing section 23. Here, it is possible to use a needle puncturing unit using a puncture needle.

Sensor cartridge 27 is removably inserted in the lower part of housing 22 in the vicinity of puncturing section 23. Sensor cartridge 27 is composed of sensor chamber 27a in which sensors 24 are stacked and stored, desiccant chamber 27c in which desiccant 27b is stored and conveying section 27d that conveys the bottom sensor 24 stored in sensor chamber 27a to puncturing section 23.

Sensors 24 stacked and stored in sensor chamber 27a are pressed downward by pressing means 27e. Pressing means 27e is biased downward by spring 27f. Desiccant 27b is stored to dry the inside of sensor chamber 27a and prevents deterioration of sensors 24. Conveying section 27d is composed of slide plate 27g that conveys sensor 24 stored on the bottom to puncturing section 23 and spring 27h that biases slide plate 27g in the direction of arrow 28a.

Negative pressure means 29 is provided above sensor cartridge 27. Negative pressure means 29 is composed of a motor and a vacuum pump coupled to this motor. A negative pressure generated in the vacuum pump is supplied to negative pressure chamber 29a (see FIG. 35A) formed in lower holder 23b. Negative pressure chamber 29 makes skin 9 (see FIG. 35A) swell by creating a negative pressure in puncturing section 23 at the time skin 9 is punctured.

Electrical circuit section 30 is accommodated between negative pressure means 29 and laser puncturing unit 26. Electrical circuit section 30 measures the blood sugar level and so forth, controls laser puncturing unit 26 and controls negative pressure means 29 based on signals transmitted from sensor 24. Battery 20 supplies power to each of those parts. Battery 20 is removably inserted in housing 22.

Now, operations of blood test apparatus 21 configured as described above will be explained.

First, puncturing operations of blood test apparatus 21 will be described.

As shown in FIG. 30, the user first slides slide plate 27g in the direction of arrow 28b. As a result of this, sensor 24 is set between upper holder 23a and lower holder 23b in puncturing section 23. Next, the user contacts lower holder 23b in puncturing section 23 with skin 9 to sample blood. In this state, the user presses puncturing button 26j (see FIG. 22). By this means, laser light 26h (see FIG. 35A) is emitted from laser puncturing unit 26 and punctures skin 9. Blood exudes from skin 9. Blood is taken into sensor 24 and chemically reacts in sensor 24, and the result is transmitted to electrical circuit section 30. Electrical circuit section 30 measures the blood sugar level and so forth based on signals transmitted from sensor 24. Electrical circuit section 30 displays the measurement result on display section 50 (see FIG. 22).

Now, operations at the time a sensor is ejected will be explained with reference to FIG. 31 to FIG. 35A and FIG. 35B.

FIG. 30 shows a state during or immediately after measurement, that is, a state in which a finger touches lower holder 23b. The state shown in FIG. 30 is referred to as the first state.

Figure 31:
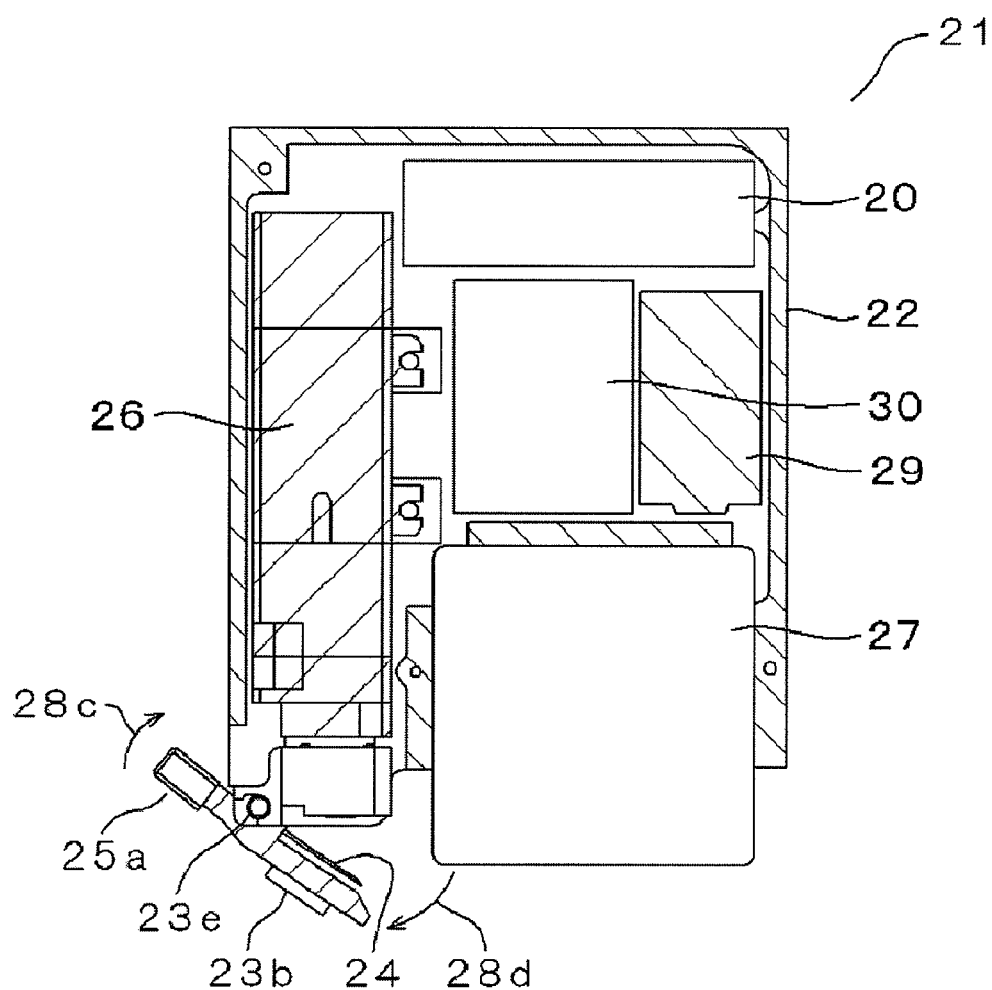
FIG. 31 is a cross sectional view showing when a sensor is ejected from the blood test apparatus according to Embodiment 4.
Figure 32:
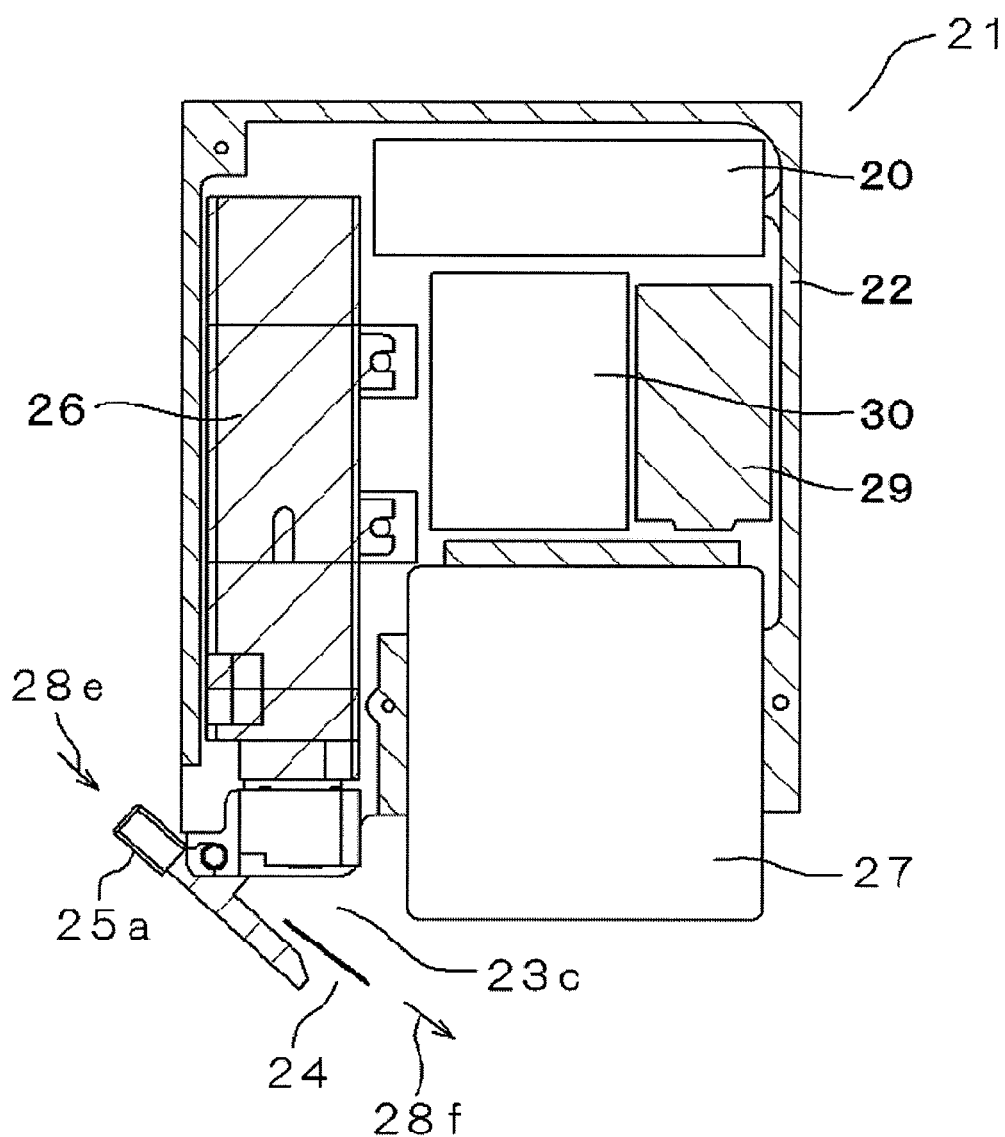
FIG. 32 is a cross sectional view showing when a sensor is ejected from the blood test apparatus according to Embodiment 4.

FIG. 31 and FIG. 32 are cross sectional views showing the blood test apparatus when a sensor is ejected. FIG. 31 shows a second state and FIG. 32 shows a third state.

As shown in FIG. 31, the user lifts ejection button 25a in the direction of arrow 28c. Lower holder 23b on which sensor 24 is placed rotates about supporting point 23e in the direction of arrow 28d.

Next, as shown in FIG. 32, the user pushes ejection button 25a in the direction of arrow 28e. Sensor 24 placed on lower holder 23b is ejected in the direction of arrow 28f. By this means, measurement of the blood sugar level and so forth is finished, and sensor 24 with blood is ejected below the sensor inserting inlet 23c side without contacting puncturing section 23 and so forth. As described above, by ejecting sensor 24 having been inserted in puncturing section 23 back to the sensor cartridge 27 side, it is possible to eject sensor 24 without staining puncturing section 23 and sensor cartridge 27 placed in the vicinity of puncturing section 23 with blood having adhered to sensor 24, so that it is possible to keep puncturing section 23 and its neighborhood clean.

In addition, sensor 24 with blood is ejected by pressing ejection button 25a in the direction of arrow 28e without directly touching sensor 24, so that fingers are not stained and are kept clean. Moreover, sensor 24 is ejected back to the sensor cartridge 27 side from which sensor 24 is inserted, so that connector terminal 18 in the connector (see FIG. 35A and FIG. 35B) provided in the leading edge side of sensor 24 contacts substrate 31 in sensor 24 and is not above spacer 32 and cover 33. Therefore, the burden on connector 18c is reduced, so that it is possible to extend the durability of insertion and extraction of a connector.

Figure 33:
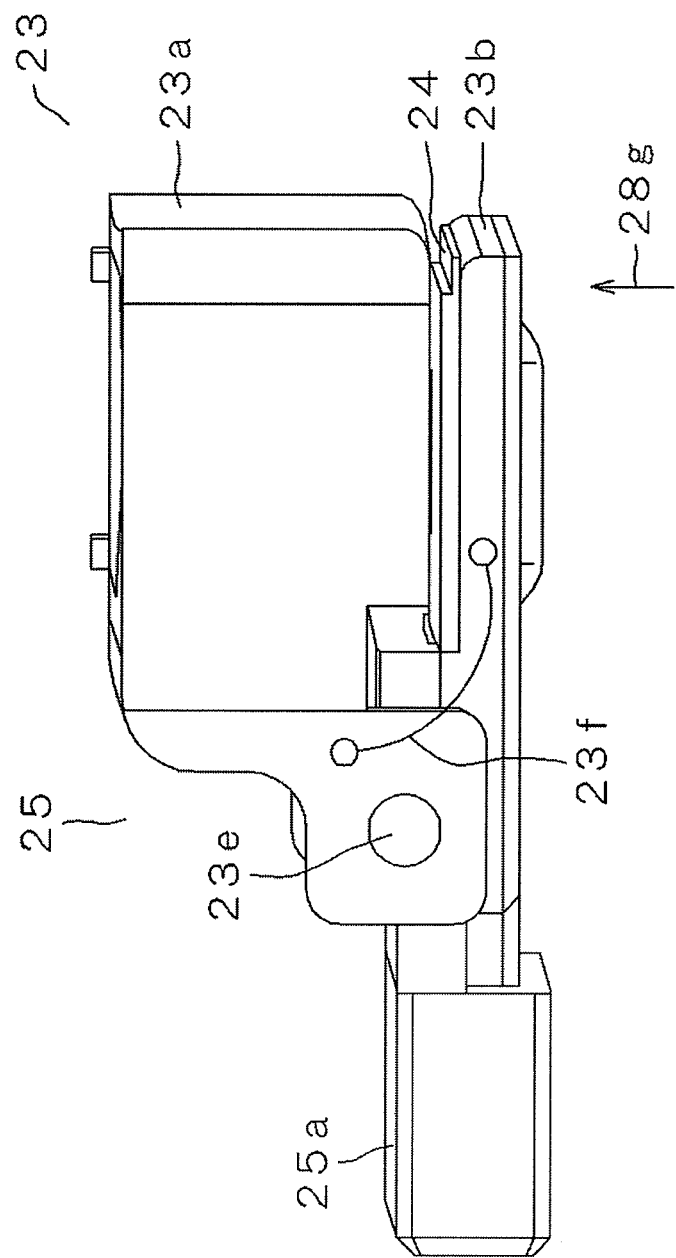
FIG. 33 is a perspective view showing a puncturing section and an ejecting means coupled to the puncturing section in the blood test apparatus according to Embodiment 4.
Figure 34:
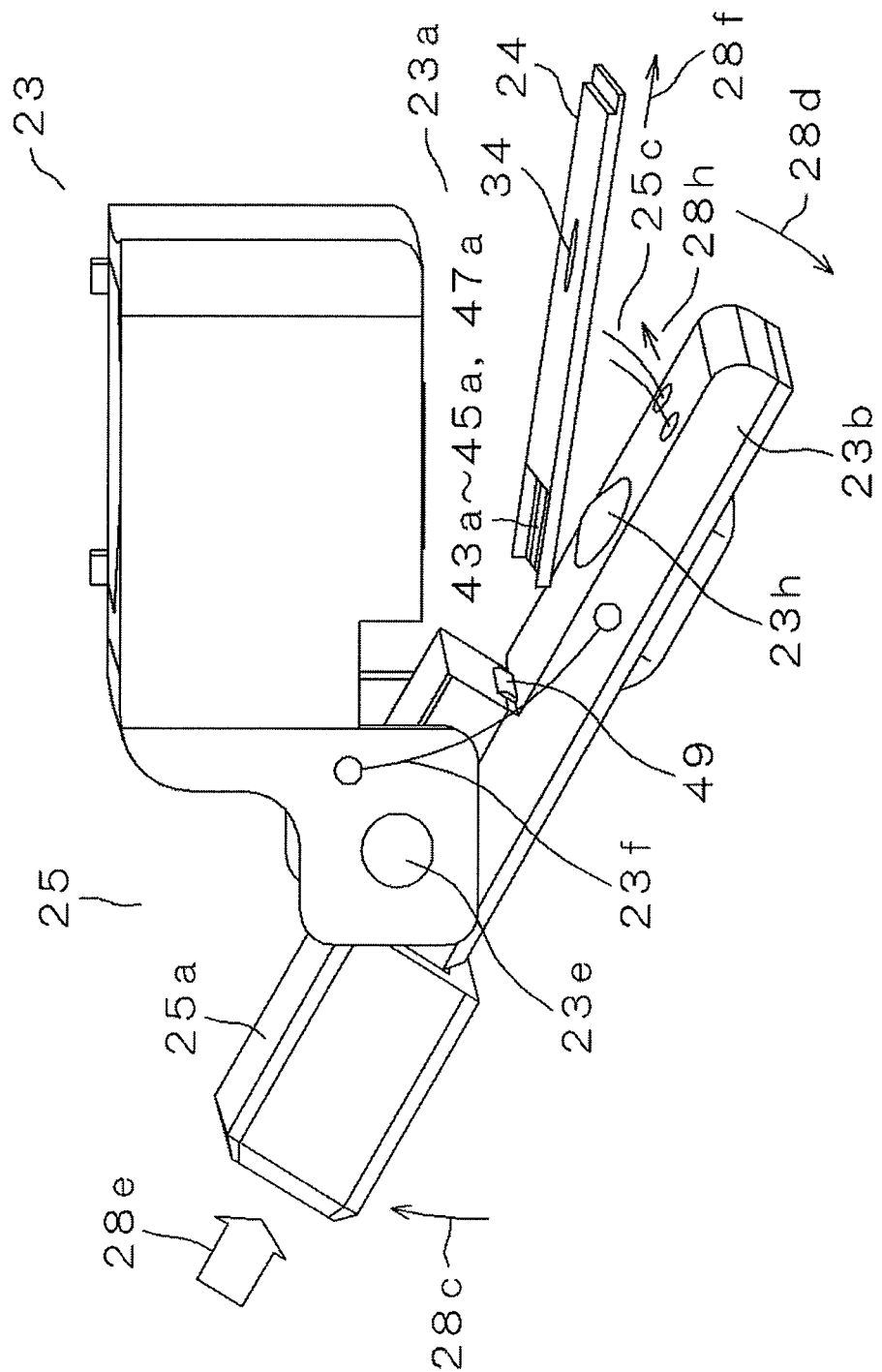
FIG. 34 is a perspective view showing a puncturing section and an ejecting means coupled to the puncturing section in the blood test apparatus according to Embodiment 4.

FIG. 33 and FIG. 34 are perspective view of puncturing section 23 and ejecting means 25 coupled to puncturing section 23.

As shown in FIG. 33, lower holder 23b constituting puncturing section 23 is biased upward (the direction of arrow 28g) by spring 23f, and sensor 24 is sandwiched and set between upper holder 23a and lower holder 23b. Then, in this state, laser puncturing unit 26 performs puncturing.

When puncturing is completed, the user lifts upward (the direction of arrow 28c) ejection button 25a constituting ejecting means 25 as shown in FIG. 34. As a result of this, lower holder 23b coupled to ejection button 25a rotates about supporting point 23e against leaf spring 23f, so that the sensor inserting inlet 23c side opens downward (the direction of arrow 28d).

In this state, the user pushes, in the direction of arrow 28e, ejection button 25a slidably provided. As a result of this, sensor 24 is pushed out to the sensor inserting inlet 23c side by two pushing members 25b (see FIG. 35A and FIG. 35B) coupled to ejection button 25a and lifted upward (the direction of arrow 28h) by lifting member 25c. Lifting member 25c bypasses storing section 34 formed in sensor 24 and projects from the top surface of lower holder 23b.

Figure 35A:
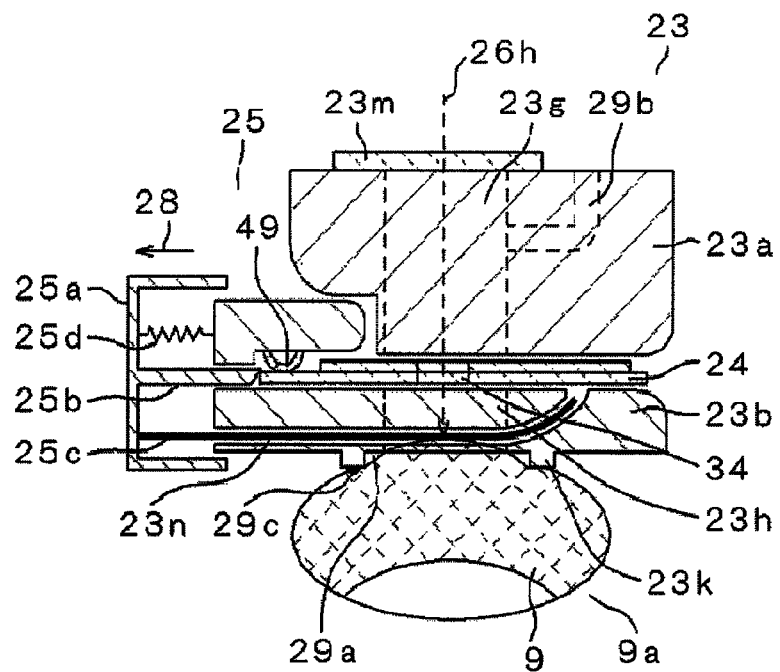
FIG. 35A is a cross sectional view showing in a state in which a finger contacts a finger rest part in the blood test apparatus according to Embodiment 4.
Figure 35B:
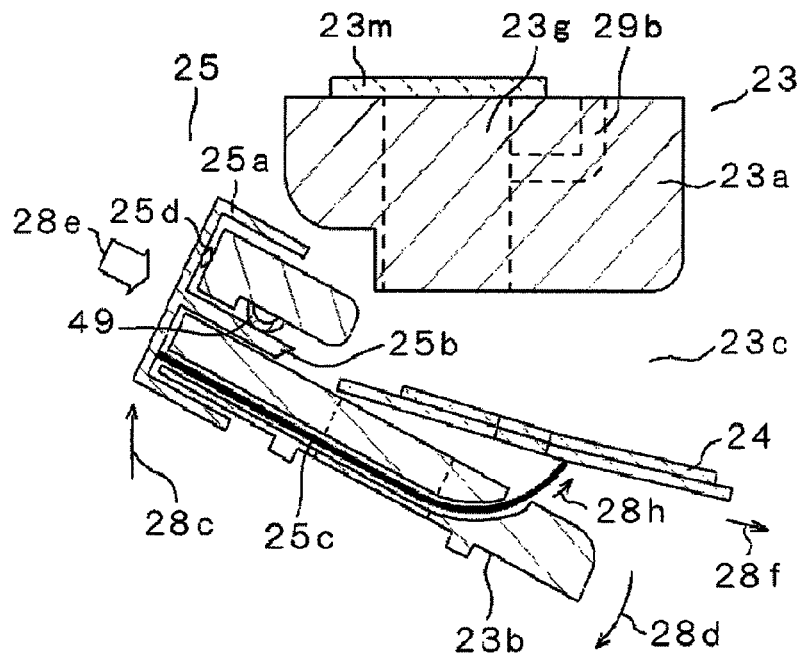
FIG. 35B is a cross sectional view showing a state in which a used sensor is discarded after measurement by the blood test apparatus according to Embodiment 4 is finished.

Here, pushing member 25b and lifting member 25c constitute a sliding mechanism to push out sensor 24 to the holding section side by being pressed by ejection button 25a. As shown in FIG. 35A and FIG. 35B, this sliding mechanism has an inclined part having a tapered surface to push out sensor 24.

As described above, the sliding mechanism has an inclined part having a tapered surface to push out sensor 24, so that it is possible to adequately press sensor 24 when sensor 24 is ejected (pushed out) and it is possible to prevent sensor 24 from dropping to improve safety.

Lifting member 25c ejects sensor 24 without being caught in storing section 34 provided in sensor 24. This allows sensor 24 to be ejected without staining puncturing section 23 with sensor 24 with blood. In addition, sensor 24 is ejected only by pressing ejection button 25a, so that fingers are not stained.

FIG. 35A and FIG. 35B are cross sectional views showing puncturing section 23 and ejecting means 25 coupled to puncturing section 23. FIG. 35A is a cross sectional view showing puncturing section 23 and ejecting means 25 shown in FIG. 33, and FIG. 35B is a cross sectional view showing puncturing section 23 and ejecting means 25 shown in FIG. 34. Here, FIG. 35A shows a state in which finger 9 contacts negative pressure chamber 29a formed in lower holder 23b.

As shown in FIG. 35A, spring 25d is mounted between ejection button 25a and lower holder 23b formed integrally with the connector and biases ejection button 25a in the direction of arrow 28j. Pushing member 25b mounted in ejection button 25a contacts the connection electrodes 43a to 45a and 47a (see FIG. 20) side formed in the neighborhood of the leading edge side of sensor 24. In addition, in this state, lifting member 25c mounted in ejection button 25a is placed in through-hole 23n formed in lower holder 23b, and, in the state shown in FIG. 35A, does not project (embedded state) from the top surface of lower holder 23b. Through-hole 23n is provided in the different position from storing section 34 formed in sensor 24 and is provided in the direction to insert sensor 24, or provided in the different direction from the direction to eject sensor 24. By this means, lifting member 25c is not caught in storing section 34. In addition, flexible steel is used for the material for lifting member 25c.

At the time skin is punctured, connection electrodes 43a to 45a and 47a formed in sensor 24 contacts connector terminal 18c. In addition, through-hole 23g penetrating upper holder 23a vertically, and through-hole 23h penetrating storing section 34 and lower holder 23b vertically are arranged on a straight line, and laser light 26h emitted from laser puncturing unit 26 passes through through-hole 23g and through-hole 23h to puncture skin 9.

Negative pressure path 29b guides a negative pressure from negative pressure means 29 to negative pressure chamber 29a. Skin 9 is made in a state of tension by applying a negative pressure to negative pressure chamber 29a, so that blood is easily sampled. Skin detecting sensor 29c is provided on bank 23k constituting negative pressure chamber 29a to detect contact with skin 9. In addition, transparent film 23m is removably provided on the top surface of through-hole 23g. Transparent film 23m is mounted in order to allow laser light 26h to pass through and not to attenuate laser light 26h due to adhesion of scattering materials to laser puncturing unit 26 at the time skin 9 is punctured. It is necessary to replace transparent film 23m on a regular basis at the time its transmittance is decreased. In addition, it is possible to improve the negative pressure performance by seal hermetically through-hole 23g with transparent film 23m.

When puncturing is completed, the user lifts ejection button 25a in the direction of arrow 28c as shown in FIG. 34 and FIG. 35B. As a result of this, lower holder 23b rotates downward (the direction of arrow 28d), so that the sensor inserting inlet 23c side opens. Next, the user presses ejection button 25a in the direction of arrow 28e against the bias of spring 25d. As a result of this, sensor 24 is pushed out from the connector by pushing member 25b and lifted upward by push-up member 25c. Then, sensor 24 is ejected in the direction of arrow 28f.

Embodiment 5

With Embodiment 5, another exemplary configuration of the ejecting means coupled to puncturing section 23 will be explained.

Figure 36A:
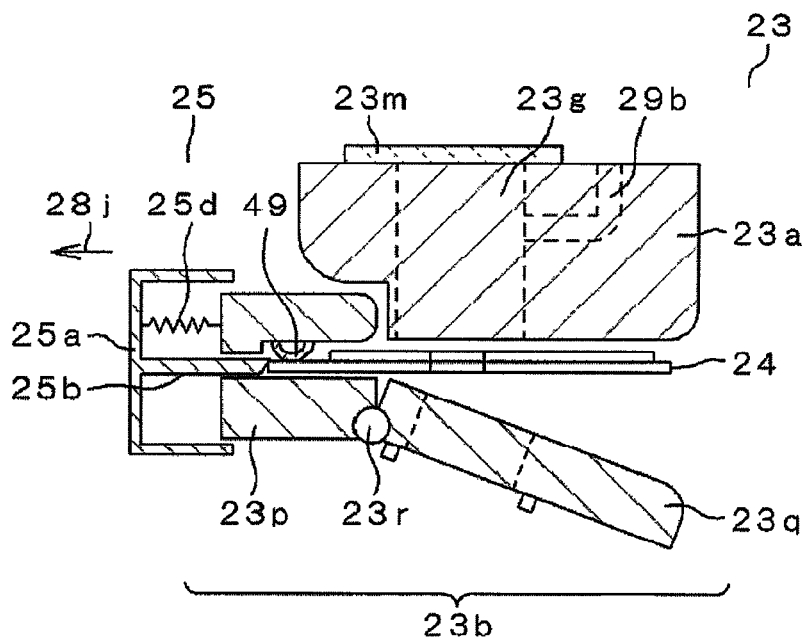
FIG. 36A is a cross sectional view showing a state in which a sensor is loaded in a blood test apparatus according to Embodiment 5 of the present invention.
Figure 36B:
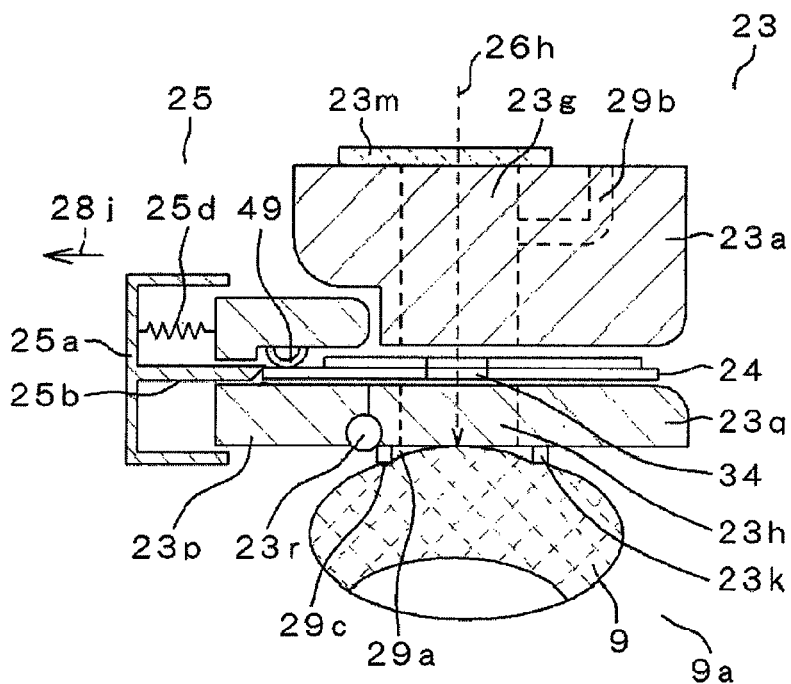
FIG. 36B is a cross sectional view showing in a state in which a finger contacts a finger rest part in the blood test apparatus according to Embodiment 5.
Figure 36C:
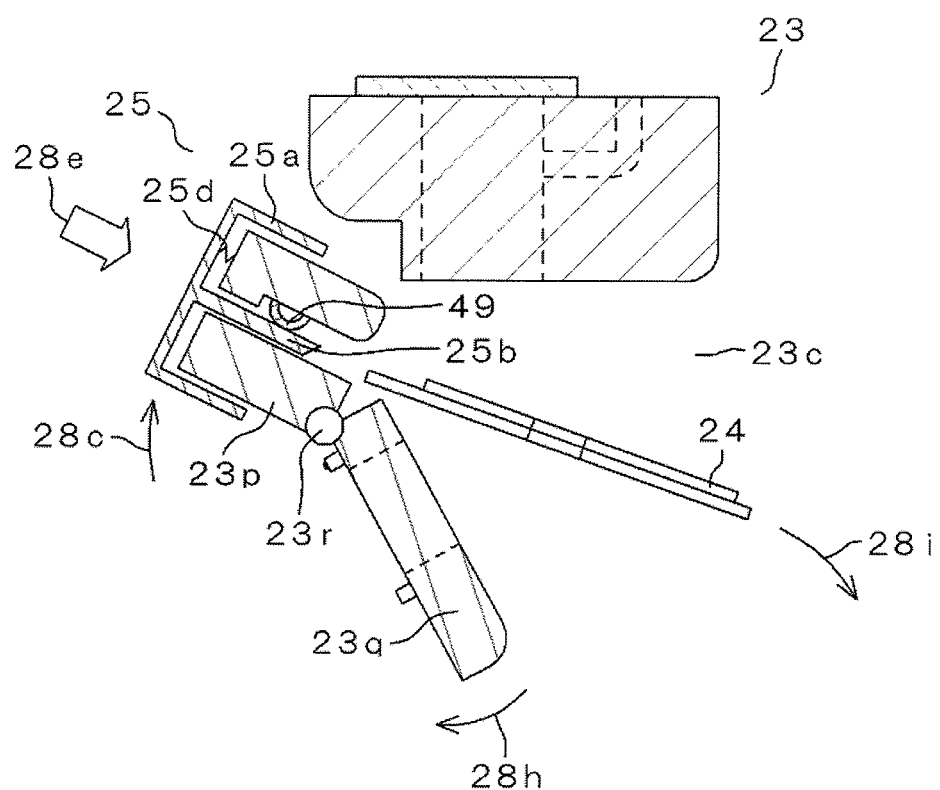
FIG. 36C is a cross sectional view showing a state in which a used sensor is discarded after measurement by the blood test apparatus according to Embodiment 5 is finished.

FIGS. 36 A-C are cross sectional views of an ejecting means coupled to puncturing section 23 in a blood test apparatus according to Embodiment 5 of the present invention. FIG. 36A is a cross sectional view showing a state in which a sensor is loaded in another exemplary puncturing section, FIG. 36B is a cross sectional view showing a state in which a finger contacts a finger rest part and FIG. 36C is a cross sectional view showing a state in which a used sensor is discarded. The same components as in FIG. 35A and FIG. 35B will be assigned the same reference numerals and overlapping descriptions will be omitted.

In puncturing section 23 according to the present embodiment, lower holder 23b is composed of finger rest part 23q that is able to rotate about supporting point 23r and lower holder-fixed part 23p, which is a fixed part.

FIG. 36A shows a state in which sensor 24 is ejected and conveyed from sensor cartridge 27 and sandwiched between upper holder 23a and lower holder-fixed part 23p constituting puncturing section 23.

As shown in FIG. 36A, spring 25d is mounted between ejection button 25a and lower holder 23b formed integrally with connector 18 and biases ejection button 25a in the direction of arrow 28j. Push-up member 25b mounted in ejection button 25a contacts the connection electrodes 43a to 45a and 47a (see FIG. 22) side formed in the neighborhood of the leading edge side of sensor 24. In addition, a plurality of connector terminals 18c are connected to connection electrodes 43a to 45a and 47a.

At this time, rotary finger rest part 23q comes down as shown in FIG. 36A and has still not contacted sensor 24.

FIG. 36B is a cross sectional view of the ejecting means coupled with puncturing section 23 showing a state in which a finger contacts the finger rest part.

Finger holding section 23q is lifted by finger 9 and rotates about supporting point 23r to contact the bottom surface of sensor 24. At this time, the bottom surface of through-hole 23h in finger rest part 23q is blocked with the surface of finger 9 to make a space in which through-hole 23h, storing section 34 in sensor 24 and through-hole 23g in upper holder 23a are connected to communicate with each other, as a negative pressure space (the dashed line zone in FIG. 36B).

A negative pressure is applied to the above-described negative pressure space via negative pressure path 29b coupled with a negative pressure means, so that the surface of finger 9 is sucked. Then, by pressing a puncturing button, laser illuminating light 26h emitted from laser puncturing unit 26 illuminates the position to puncture in the finger and punctures the position.

After puncturing, blood exuding on the surface of skin 9 is stored in storing section 34 by the above-described negative pressure, and then, introduced to the supply path in sensor 24 by capillary action, and measured and tested. The measurement result is displayed on a display section.

FIG. 36C is a cross sectional view of the ejecting means coupled to puncturing section 23 showing a state in which used sensor 24 is discarded after measurement is completed.

When finger 9 is removed from finger rest part 23q after the above-described measurement is completed, rotary finger holding section 23q leaves the bottom surface of sensor 24 (the same state as in FIG. 36A).

Then, the user lifts ejection button 25a upward (the direction of arrow 28c) to tilt lower holder 23b and ejecting means 25 downward and pushes ejection button 25a in the direction of arrow 28e, so that pushing member 25b ejects and discards sensor 24 in the direction of arrow 28i.

At this time, finger rest part 23q forming lower holder 23b has already been rotated to a position apart from sensor 24 before sensor 24 is ejected, so that there is no concern about adhesion of stain from a used sensor and so forth, and safety is provided.

As described above, according to the present embodiment, blood test apparatus 21 rotates lower holder 23b and finger rest part 23q in lower holder 23b downward to form spaces between sensor 24 and upper holder 23a and between sensor 24 and lower holder 23b, respectively, and ejects sensor 24 in this state, so that it is possible to eject sensor 24 without allowing contact of blood having adhered to sensor 24 with puncturing section 13, sensor cartridge 27 and so forth. Therefore, puncturing section 23 is not stained with blood having adhered to sensor 24, so that it is possible to keep puncturing section 23 and its neighborhood clean.

In addition, sensor 24 with blood is ejected using ejecting means 25 without directly touching sensor 24 with fingers, so that fingers are not stained with blood and kept clean, and therefore, sanitation and safety are provided.

Embodiment 6

Figure 37:
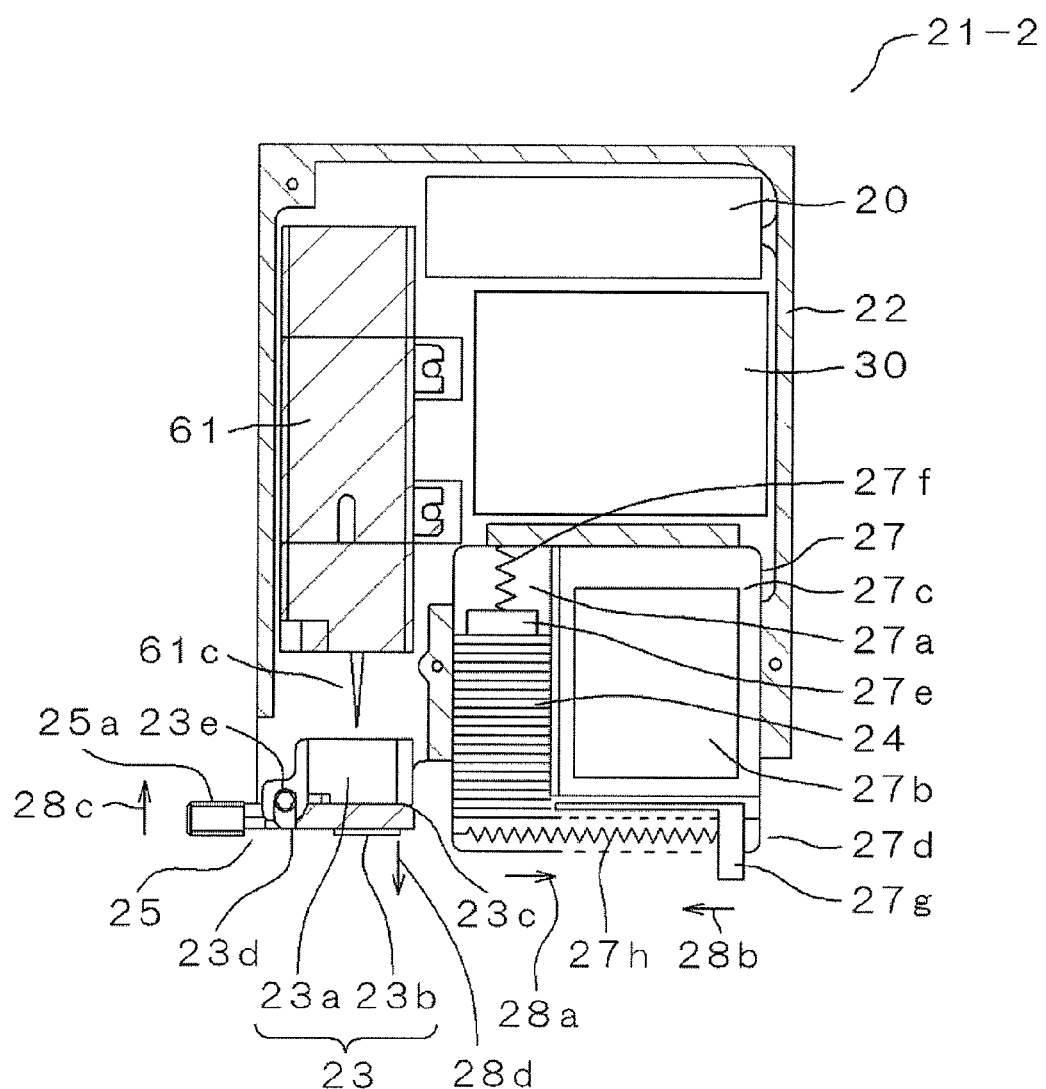
FIG. 37 is a cross sectional view of a blood test apparatus according to Embodiment 6 of the present invention.

FIG. 37 is a cross sectional view of blood test apparatus 21-2 according to Embodiment 6 of the present invention. The same components as in FIG. 30 will be assigned the same reference numerals and overlapping descriptions will be omitted.

With the present embodiment, needle puncturing unit 61 is used as a puncturing means instead of laser puncturing unit 26 shown in FIG. 30.

As shown in FIG. 37, blood test apparatus 21-2 has housing 22 made of resin and having an approximately rectangular solid shape. Puncturing section 23 is mounted in a lower corner of housing 22. Puncturing section 23 is composed of upper holder 23a and lower holder 23b, and sandwiches and fixes sensor 24 between upper holder 23a and lower holder 23b.

Lower holder 23b is provided with supporting point 23e in the neighborhood of end 23d up to which sensor 24 is inserted, and formed to be able to rotate downward (the direction of arrow 28d) about supporting point 23e.

Ejection button 25a constituting ejecting means 25 is slidably coupled to the neighborhood of end 23d up to which lower holder 23b is inserted. By rotating ejection button 25a upward (the direction of arrow 28c), the sensor insertion inlet 23c side, which is the sensor cartridge 27 side of lower holder 23b, rotates downward.

Needle puncturing unit 61 is provided to face puncturing section 23. Sensor cartridge 27 is removably inserted in the lower part of housing 22 next to puncturing section 23. Sensor cartridge 27 is composed of sensor chamber 27a in which sensors are stacked and stored, desiccant chamber 27c in which desiccant 27b is stored and conveying section 27d that conveys the bottom sensor 24 stored in sensor chamber 27a to puncturing section 23.

Sensors 24 stacked and stored in sensor chamber 27a are pressed downward by pressing means 27e. Pressing means 27e is biased downward by spring 27f. Desiccant 27b is stored to dry the inside of sensor chamber 27a and prevents deterioration of sensors 24. Conveying section 27d is composed of slide plate 27g that conveys sensor 24 stored on the bottom to puncturing section 23 and spring 27h that biases slide plate 27g in the direction of arrow 28a.

Electrical circuit section 30 is accommodated above sensor cartridge 27. This electrical circuit section 30 measures the blood sugar level and so forth based on signals transmitted from sensor 24.

With blood test apparatus 21-2 configured as described above, the user first slides slide plate 27g in the direction of arrow 28b. As a result of this, sensor 24 is set between upper holder 23a and lower holder 23b in puncturing section 23. Next, the user contacts lower holder 23b in puncturing section 23 with skin 9 to sample blood from. In this state, puncturing button 26j (see FIG. 22) is pressed. As a result of this, puncture needle 61c provided in needle puncturing unit 61 moves downward and punctures skin 9. Blood exudes from skin 9. Blood is taken into sensor 24 and chemically reacts in sensor 24, and the result is transmitted to electrical circuit section 30. Electrical circuit section 30 measures the blood sugar level and so forth based on signals transmitted from sensor 24. Electrical circuit section 30 displays the measurement result on display section 50 (see FIG. 22).

As described above, the configuration is the same as Embodiment 5 except for the puncturing means. Therefore, it is possible to provide the same effect as in Embodiment 5.

The above description is illustration of preferred embodiments of the present invention and the scope of the invention is not limited to this.

Although the names "blood sensor" and "blood test apparatus" are used in the apparatus of the invention for ease of explanation, "biosensor", "blood analysis apparatus", "puncturing apparatus" and so forth are possible. Generally, the names vary depending on the types of blood samples.

In addition, the number, the arrangement (position, interval and so forth) and the shape (circle, arc, concentric circle and so forth) of each of parts constituting a sensor, such as skin detecting electrodes, are not limited, and the shape (with or without a hole), the structure (stacking order of each sensor component) and the electrode structure (through-hole interconnection and so forth) of a sensor are also not limited.

In the same way, the type, the number, the connection method and so forth of each of parts constituting the above-described blood test apparatus, such as a laser puncturing means, are not limited.

The disclosure of Japanese Patent Application No. 2008-058950, filed on Mar. 10, 2008, including the specification, drawings and abstract, is incorporated herein by reference in its entirety.

INDUSTRIAL APPLICABILITY

The blood test apparatus according to the present invention does not stain puncturing section, its neighborhood, a finger to use and so forth with blood and therefore is applicable to a puncturing apparatus and so forth in safety. It is applicable to a blood test apparatus that samples blood from skin by a blood sampling means and analyzes blood components. Moreover, it is possible to make good use of exuding blood and provide sanitation by replacing sensors, so that the blood test apparatus is applicable to a puncturing apparatus and so forth.

What is claimed is:

1. A blood test apparatus comprising:
a first holding section composed of a first holder and a second holder that are configured to sandwich a blood sensor therebetween;
a second holding section that is configured to hold the blood sensor sandwiched between the first holder and the second holder; and
a puncturing section that punctures skin from a first holder side of the blood sensor sandwiched between the first holder and the second holder, wherein;
the second holding section is rotatable around a rotation axis while holding the blood sensor,
the second holder is rotatable around the rotation axis so as to define a space between the first holder and the second holder, and
the second holding section is pivotably mounted on a rotating shaft that is coaxial with the second holder.

2. The blood test apparatus according to claim 1, wherein the puncturing section is configured to penetrate the blood sensor to puncture the skin.

3. The blood test apparatus according to claim 1, wherein the first holder is fixed to a housing, and
the second holder faces the first holder and is pivotably mounted on a rotating shaft of the housing.

4. The blood test apparatus according to claim 1, wherein the first holder is fixed to a housing, and
the second holder faces the first holder and is pivotably mounted on a rotating shaft of the first holder.

5. The blood test apparatus according to claim 1, wherein the second holding section is pivotably mounted on a rotating shaft of a housing.

6. The blood test apparatus according to claim 1, wherein the second holding section is pivotably mounted on a rotating shaft of the first holder.

7. The blood test apparatus according to claim 1, wherein the second holding section has a sliding mechanism that is configured to release a holding of the blood sensor when the second holder rotates.

8. The blood test apparatus according to claim 7, wherein the sliding mechanism includes an inclined part having a tapered surface to push the blood sensor.

9. The blood test apparatus according to claim 1, wherein
the second holding section is pivotably mounted on a rotating shaft of a housing; and
when the second holding section rotates by a predetermined angle, the second holder rotates by an angle greater than the predetermined angle of the second holding section.

10. The blood test apparatus according to claim 1, further comprising:
a sensor cartridge in which blood sensors are stacked and stored; and
a conveying section that conveys the blood sensors stacked and stored in the sensor cartridge to the puncturing section.

11. The blood test apparatus according to claim 1, further comprising:
a pushing section provided in the second holder and configured to push the blood sensor so as to release a holding of the blood sensor; and
an ejecting button which is configured to operate the pushing section.

12. The blood test apparatus according to claim 11, wherein the pushing section includes a lifting section that is configured to lift the blood sensor from the second holder.

13. The blood test apparatus according to claim 11, wherein the pushing section has an inclined part having a tapered surface to push the blood sensor.

14. The blood test apparatus according to claim 12, wherein when the the second holder rotates, the lifting section separates the blood sensor from a contact surface of the second holder.

15. The blood test apparatus according to claim 1, further comprising a negative pressure section that is configured to swell the skin to be punctured by the puncturing section by applying a negative pressure.

16. The blood test apparatus according to claim 15, wherein the negative pressure section has a negative pressure path coupled to the first holder.

17. The blood test apparatus according to claim 1, wherein the puncturing section is a laser puncturing unit that is configured to puncture the skin with laser light.

18. The blood test apparatus according to claim 1, wherein the puncturing section is a needle puncturing unit that is configured to puncture the skin with a needle.

19. The blood test apparatus according to claim 11, wherein
the first holder is fixed to a housing,
the second holder faces the first holder and is pivotably mounted on a rotating shaft of the housing, and
the rotating shaft is provided between the ejecting button and each of the first holder and the second holder.

20. The blood test apparatus according to claim 19, wherein
the ejecting button is disposed outside of the housing.

21. A blood test apparatus comprising:
a holding section composed of a first holder and a second holder that sandwich and hold a blood sensor therebetween;
a puncturing section that punctures skin from a first holder side of the blood sensor held by the holding section; and
an ejecting section that rotates the second holder to part from the first holder and defines a space between the first holder and the second holder by the rotation to expose the blood sensor,
wherein the ejecting section includes an ejection button that is coupled to the second holder and provided to slidably move, and a pushing section that is coupled to the ejection button and pushes the blood sensor,
the ejecting section includes a lifting section that is coupled to the ejection button and lifts the blood sensor, and
when the blood sensor is ejected, the lifting section separates the blood sensor from a contact surface of the second holder.

* * * * *